US008048427B2

(12) United States Patent
Pang et al.

(10) Patent No.: US 8,048,427 B2
(45) Date of Patent: *Nov. 1, 2011

(54) SUBGENOMIC REPLICONS OF THE FLAVIVIRUS DENGUE

(75) Inventors: Xiaowu Pang, Rockville, MD (US); Andrew I. Dayton, Knoxville, MD (US); Mingjie Zhang, Bethesda, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/394,822

(22) Filed: Feb. 27, 2009

(65) Prior Publication Data

US 2010/0233210 A1    Sep. 16, 2010

Related U.S. Application Data

(63) Continuation of application No. 10/656,721, filed on Sep. 5, 2003, now Pat. No. 7,524,508, which is a continuation of application No. PCT/US02/06962, filed on Feb. 21, 2002.

(60) Provisional application No. 60/274,684, filed on Mar. 9, 2001.

(51) Int. Cl.
*A61K 39/12* (2006.01)
*C12N 7/01* (2006.01)
*C12N 15/86* (2006.01)

(52) U.S. Cl. ............... 424/199.1; 424/205.1; 424/218.1; 435/235.1; 435/320.1

(58) Field of Classification Search ........................ None
See application file for complete search history.

(56) References Cited

U.S. PATENT DOCUMENTS 7,524,508 B2 *  4/2009  Pang et al. ................. 424/205.1

FOREIGN PATENT DOCUMENTS

WO         99/28487 A1    6/1999

OTHER PUBLICATIONS

Behrens set al., "Characterization of an Autonomous Subgenomic Pestivirus RNA Replicon", Journal of Virology, 72 (3), pp. 2364-2372 (1998).
Fields et al., Virology, Third Edition, pp. 931-937 (1996).
Varnavski et al., "Noncytopathic Flavivirus Replicon RNA-Based System for Expression and Delivery of Heterologous Genes", Virology, vol. 255, pp. 366-375 (1999).
Khromykh et al., "cis- and trans-acting Elements in Flavivirus RNA Replication", Journal of Virology, 74(7), pp. 3253-3263 (2000).
Proutski et al., "Biological consequences of deletions within the 3'-untraslated region of flaviviruses may be due to rearrangements of RNA secondary structure", Virus Research 64, pp. 107-123 (1999).
Corver et al., "Fine Mapping of a cis-acting Sequence Element in Yellow Fever Virus RNA that is Required for RNA Replication and Cyclization", Journal of Virology, 77(3), pp. 2265-2270 (2003).
Khromykh et al., Journal of Virology, vol. 71, pp. 1497-1505 (1997).
Khromykh (Current Opinion in Molecular Therapeutics) 2(5), pp. 555-569 (2000).
Polo et al., Journal of Virology, vol. 71, pp. 5366-5374 (1997).
Fields et al., Virology—Third Edition, pp. 931-937 (1996).
C. Beard et al., "Development of DNA vaccines for foot-and-mouth disease, evaluation of vaccines encoding replicating and non-replicating nucleic acids in swine", J. Biotechnol., vol. 73, pp. 243-249 (1999).
N. Bhamarapravati et al., "Live attenuated tetravalent dengue vaccine", Vaccine—18 Suppl, vol. 2, pp. 44-47 (2000).
M.A. Brinton et al., "Immune mediated and inherited defenses against flaviviruses", Clin. Diagn. Virol., vol. 10, pp. 129-139 (1998).
M.J. Cardosa et al, "Dengue vaccine design: issues and challenges", Br. Med. Bull., 54(2), pp. 395-405 (1998).
T.J. Chambers et al, "Vaccine development against dengue and Japanese encephalitis: report of a World Health Organization meeting", Vaccine, 15(14), pp. 1494-1502 (1997).
T.J. Chambers et al, "Flavivirus Genome Organization, Expression and Replication", Ann Rev Microbiol, vol. 44, pp. 649-688 (1990).
B. Falgout et al., "Immunization of mice with recombinant vaccinia virus expressing authentic dengue virus nonstructural protein NSl protects against lethal Dengue virus encephalitis", J. Virol., vol. 64, pp. 4356-4363 (1990).
S.B. Halstead et al., "Pathogenesis of Dengue: Challenges to Molecular Biology", Science, vol. 239, pp. 476-481 (1988).
F.X. Heinz et al., "Epitope Mapping of Flavivirus Glycoproteins", Adv. Virus Res., vol. 31, pp. 103-168 (1986).
E.A. Henchal et al., "Synergistic Interactions of Anti-NS1 Monoclonal Antibodies Protect Passively Immunized Mice From Lethal Challenge with Dengue 2 Virus", J. Gen. Virol., vol. 69, pp. 2101-2107 (1988).
K. Irie et al., "Dengue virus type 2 compelte genome", NCB1 Database Accession No. M29095 (1993).
N. Kanesa-Thasan et al., "Safety and Immunogenicity of Attenuated Dengue Virus Vaccines (Aventis Pasteur) in Human Volunteers", Vaccine, vol. 19, pp. 3179-3188 (2001).
X. Pang et al., "Development of Dengue Virus Replicons Expressing HIV-1 gp120 and Other Heterologous Genes: A Potential Future Tool for Dual Vaccination Against Dengue Virus and HIV", BMC Microbiology, 1(28), pp. 1-9 (2002).
X. Pang et al., "Development of Dengue Virus Type 2 Replicons Capable of Prolonged Expression in Host Cells", BMC Microbiology, 1(18), pp. 1-7 (2002).

* cited by examiner

*Primary Examiner* — Mary E Mosher
(74) *Attorney, Agent, or Firm* — Edwards Angell Palmer & Dodge LLP; Peter F. Corless

(57) ABSTRACT

The present invention discloses the construction of dengue virus subgenomic replicons containing large deletions in the structural region (C-preM-E) of the genome, which replicons are useful as vaccines to protect against dengue virus infection.

31 Claims, 9 Drawing Sheets

FIG. 1   Construction of Dengue Relicon
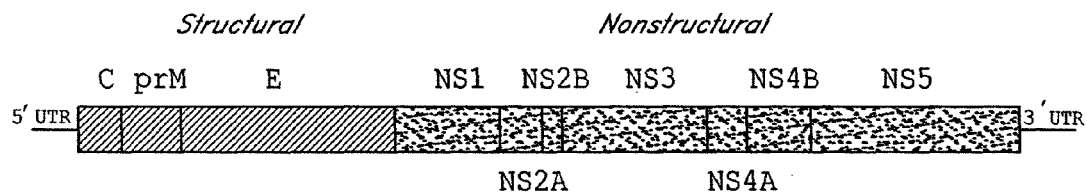
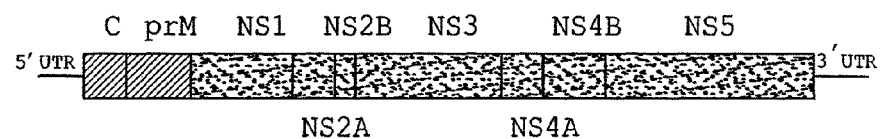
Δ E Replicon
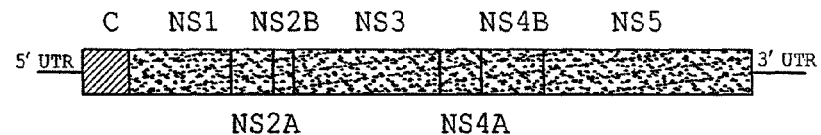
Δ ME Replicon
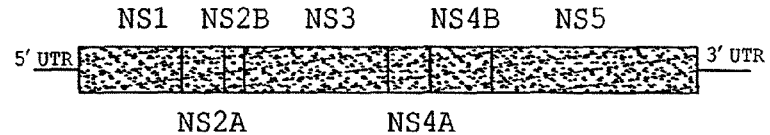
Δ CME Replicon

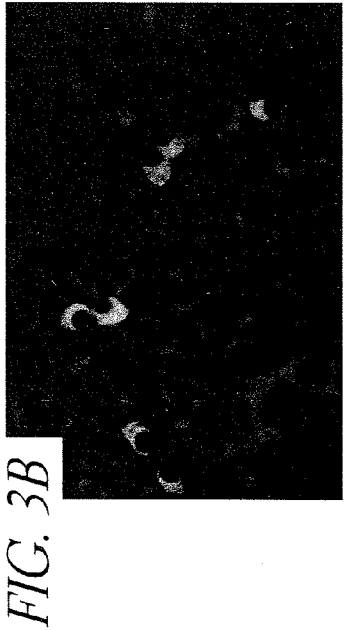
FIG. 3B
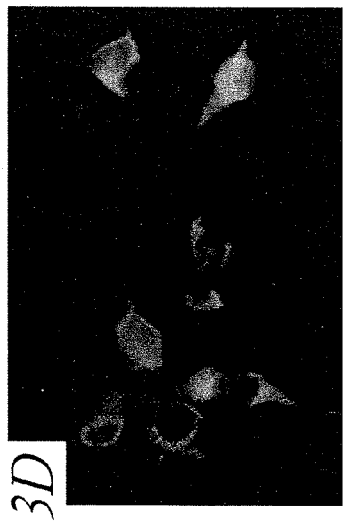
FIG. 3D
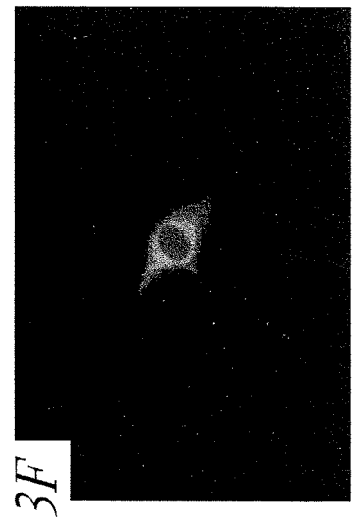
FIG. 3F
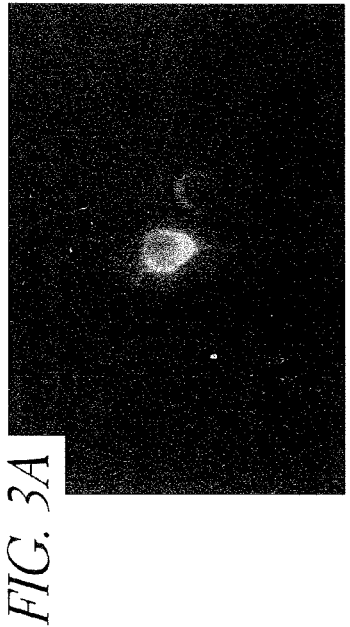
FIG. 3A
FIG. 3C
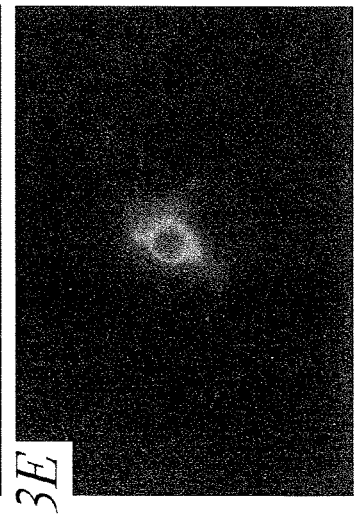
FIG. 3E

FIG. 6

```
                              SEQUENCE LISTING

<160> NUMBER OF SEQ ID NOS: 31

<210> SEQ ID NO 1
<211> LENGTH: 6
<212> TYPE: DNA
<213> ORGANISM: Artificial Sequence
<220> FEATURE:
<223> OTHER INFORMATION: Delta ME Replicon

<400> SEQUENCE: 1 agttgt                                                              6
```

```
<210> SEQ ID NO 2
<211> LENGTH: 12
<212> TYPE: DNA
<213> ORGANISM: Artificial Sequence
<220> FEATURE:
<223> OTHER INFORMATION: Delta ME Replicon

<400> SEQUENCE: 2
cgtaacagca cc                                                            12

<210> SEQ ID NO 3
<211> LENGTH: 6
<212> TYPE: DNA
<213> ORGANISM: Artificial Sequence
<220> FEATURE:
<223> OTHER INFORMATION: Delta ME Replicon

<400> SEQUENCE: 3 ggttct                                                                    6

<210> SEQ ID NO 4
<211> LENGTH: 6
<212> TYPE: DNA
<213> ORGANISM: Artificial Sequence
<220> FEATURE:
<223> OTHER INFORMATION: Delta CME Replicon

<400> SEQUENCE: 4 agttgt                                                                    6

<210> SEQ ID NO 5
<211> LENGTH: 12
<212> TYPE: DNA
<213> ORGANISM: Artificial Sequence
<220> FEATURE:
<223> OTHER INFORMATION: Delta CME Replicon

<400> SEQUENCE: 5
gagagaagca cc                                                            12

<210> SEQ ID NO 6
<211> LENGTH: 6
<212> TYPE: DNA
<213> ORGANISM: Artificial Sequence
<220> FEATURE:
<223> OTHER INFORMATION: Delta CME Replicon

<400> SEQUENCE: 6 ggttct                                                                    6

<210> SEQ ID NO 7
<211> LENGTH: 16
<212> TYPE: PRT
<213> ORGANISM: Artificial Sequence
<220> FEATURE:
<223> OTHER INFORMATION: Peptide from Mengo virus, strain M

<400> SEQUENCE: 7

Gly Tyr Phe Ser Asp Leu Leu Ile His Asp Val Glu Thr Asn Pro Gly
 1               5                  10                  15

<210> SEQ ID NO 8
<211> LENGTH: 8
<212> TYPE: PRT
<213> ORGANISM: Artificial Sequence
<220> FEATURE:
<223> OTHER INFORMATION: Peptide from Mengo virus, strain M
```

```
<400> SEQUENCE: 8

Pro Phe Thr Phe Lys Pro Arg Gln
 1               5

<210> SEQ ID NO 9
<211> LENGTH: 16
<212> TYPE: PRT
<213> ORGANISM: Artificial Sequence
<220> FEATURE:
<223> OTHER INFORMATION: Peptide from encephalomyocarditis virus, strain
      B

<400> SEQUENCE: 9

Gly Tyr Phe Ala Asp Leu Leu Ile His Asp Ile Glu Thr Asn Pro Gly
 1               5                  10                  15

<210> SEQ ID NO 10
<211> LENGTH: 8
<212> TYPE: PRT
<213> ORGANISM: Artificial Sequence
<220> FEATURE:
<223> OTHER INFORMATION: Peptide from encephalomyocarditis virus, strain
      B

<400> SEQUENCE: 10

Pro Phe Met Ala Lys Pro Lys Lys
 1               5

<210> SEQ ID NO 11
<211> LENGTH: 16
<212> TYPE: PRT
<213> ORGANISM: Artificial Sequence
<220> FEATURE:
<223> OTHER INFORMATION: Peptide from encephalomyocarditis virus, strain
      Rueckert

<400> SEQUENCE: 11

Gly Tyr Phe Ala Asp Leu Leu Ile His Asp Ile Glu Thr Asn Pro Gly
 1               5                  10                  15

<210> SEQ ID NO 12
<211> LENGTH: 8
<212> TYPE: PRT
<213> ORGANISM: Artificial Sequence
<220> FEATURE:
<223> OTHER INFORMATION: Peptide from encephalomyocarditis virus, strain
      Rueckert

<400> SEQUENCE: 12

Pro Phe Met Phe Arg Pro Arg Lys
 1               5

<210> SEQ ID NO 13
<211> LENGTH: 16
<212> TYPE: PRT
<213> ORGANISM: Artificial Sequence
<220> FEATURE:
<223> OTHER INFORMATION: Peptide from Theilers murine encephalomyelitis
      virus, bean

<400> SEQUENCE: 13

Asp Tyr Tyr Arg Gln Arg Leu Ile His Asp Val Glu Thr Asn Pro Gly
 1               5                  10                  15

<210> SEQ ID NO 14
<211> LENGTH: 8
<212> TYPE: PRT
<213> ORGANISM: Artificial Sequence
```

```
<220> FEATURE:
<223> OTHER INFORMATION: Peptide from Theilers murine encephalomyelitis
      virus, bean

<400> SEQUENCE: 14

Pro Val Gln Ser Val Phe Gln Pro
1               5

<210> SEQ ID NO 15
<211> LENGTH: 16
<212> TYPE: PRT
<213> ORGANISM: Artificial Sequence
<220> FEATURE:
<223> OTHER INFORMATION: Peptide from Theilers murine encephalomyelitis
      virus, GDVII

<400> SEQUENCE: 15

Asp Tyr Tyr Lys Gln Arg Leu Ile His Asp Val Glu Met Asn Pro Gly
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Peptide from Theilers murine encephalomyelitis
      virus, GDVII

<400> SEQUENCE: 16

Pro Val Gln Ser Val Phe Gln Pro
1               5

<210> SEQ ID NO 17
<211> LENGTH: 16
<212> TYPE: PRT
<213> ORGANISM: Artificial Sequence
<220> FEATURE:
<223> OTHER INFORMATION: Peptide from foot-and-mouth disease virus,
      strain 01 Kaufbeuren

<400> SEQUENCE: 17

Asn Phe Asp Leu Leu Lys Leu Ala Gly Asp Val Glu Ser Asn Pro Gly
1               5                   10                  15

<210> SEQ ID NO 18
<211> LENGTH: 8
<212> TYPE: PRT
<213> ORGANISM: Artificial Sequence
<220> FEATURE:
<223> OTHER INFORMATION: Peptide from foot-and-mouth disease virus,
      strain 01 Kaufbeuren

<400> SEQUENCE: 18

Pro Phe Phe Phe Ser Asp Val Arg
1               5

<210> SEQ ID NO 19
<211> LENGTH: 16
<212> TYPE: PRT
<213> ORGANISM: Artificial Sequence
<220> FEATURE:
<223> OTHER INFORMATION: Peptide from bovine rotavirus type C

<400> SEQUENCE: 19

Gln Ile Asp Arg Ile Leu Ile Ser Gly Asp Ile Glu Leu Asn Gly Pro
1               5                   10                  15

<210> SEQ ID NO 20
```

```
<211> LENGTH: 8
<212> TYPE: PRT
<213> ORGANISM: Artificial Sequence
<220> FEATURE:
<223> OTHER INFORMATION: Peptide from bovine rotavirus type C

<400> SEQUENCE: 20

Pro Asn Ala Leu Val Lys Leu Asn
 1               5

<210> SEQ ID NO 21
<211> LENGTH: 16
<212> TYPE: PRT
<213> ORGANISM: Artificial Sequence
<220> FEATURE:
<223> OTHER INFORMATION: Peptide from porcine rotavirus type C

<400> SEQUENCE: 21

Gln Ile Asp Arg Ile Leu Ile Ser Gly Asp Val Glu Leu Asn Pro Gly
 1               5                   10                  15

<210> SEQ ID NO 22
<211> LENGTH: 8
<212> TYPE: PRT
<213> ORGANISM: Artificial Sequence
<220> FEATURE:
<223> OTHER INFORMATION: Peptide from porcine rotavirus type C

<400> SEQUENCE: 22

Pro Asp Pro Leu Ile Arg Leu Asn
 1               5

<210> SEQ ID NO 23
<211> LENGTH: 69
<212> TYPE: DNA
<213> ORGANISM: Artificial Sequence
<220> FEATURE:
<223> OTHER INFORMATION: 5' primer

<400> SEQUENCE: 23
atcattatgc tgattccaac agtgatggcg ttccatttaa ccacacgtaa cagcacctca      60
ctgtctgtg                                                              69

<210> SEQ ID NO 24
<211> LENGTH: 69
<212> TYPE: DNA
<213> ORGANISM: Artificial Sequence
<220> FEATURE:
<223> OTHER INFORMATION: 5' primer

<400> SEQUENCE: 24
acagctgtcg ctccttcaat gacaatgcgt tgcataggaa tatcaaatag aagcacctca      60
ctgtctgtg                                                              69

<210> SEQ ID NO 25
<211> LENGTH: 51
<212> TYPE: DNA
<213> ORGANISM: Artificial Sequence
<220> FEATURE:
<223> OTHER INFORMATION: 3' primer

<400> SEQUENCE: 25
atacagcgtc acgactccca ccaatactag tgacacagac agtgaggtgc t               51

<210> SEQ ID NO 26
<211> LENGTH: 72
```

<212> TYPE: DNA
<213> ORGANISM: Artificial Sequence
<220> FEATURE:
<223> OTHER INFORMATION: 5' primer

<400> SEQUENCE: 26
cgaaaaaagg cgagaaatac gcctttcaat atgctgaaac gcgagagaat ggtgagcaag     60
ggcgaggagc tg                                                        72

<210> SEQ ID NO 27
<211> LENGTH: 42
<212> TYPE: DNA
<213> ORGANISM: Artificial Sequence
<220> FEATURE:
<223> OTHER INFORMATION: 3' primer

<400> SEQUENCE: 27
aaggtcaaaa ttcaacagct gcttgtacag ctcgtccatg cc                        42

<210> SEQ ID NO 28
<211> LENGTH: 74
<212> TYPE: DNA
<213> ORGANISM: Artificial Sequence
<220> FEATURE:
<223> OTHER INFORMATION: 5' primer

<400> SEQUENCE: 28
atcattatgc tgaatccaac agtgatggcg ttccatttac cacacgtaac atgagagtga     60
tggggatcag gaag                                                      74

<210> SEQ ID NO 29
<211> LENGTH: 45
<212> TYPE: DNA
<213> ORGANISM: Artificial Sequence
<220> FEATURE:
<223> OTHER INFORMATION: 3' primer

<400> SEQUENCE: 29
aaggtcaaaa ttcaacagct gggtgggtgc taatcctaat ggttc                     45

<210> SEQ ID NO 30
<211> LENGTH: 60
<212> TYPE: DNA
<213> ORGANISM: Artificial Sequence
<220> FEATURE:
<223> OTHER INFORMATION: 5' primer

<400> SEQUENCE: 30
cagctgttga attttgacct tcttaagctt gcgggagacg tcgagtccaa ccctggcccc     60

<210> SEQ ID NO 31
<211> LENGTH: 72
<212> TYPE: DNA
<213> ORGANISM: Artificial Sequence
<220> FEATURE:
<223> OTHER INFORMATION: 3' primer

<400> SEQUENCE: 31
atacagcgtc acgactccca ccaatactag tgacacagac agtgaggtgc tggggccagg     60
gttggactcg ac                                                        72

SUBGENOMIC REPLICONS OF THE FLAVIVIRUS DENGUE

RELATED APPLICATIONS

This application is a continuation of U.S. patent application Ser. No. 10/656,721, filed Sep. 5, 2003, which is a continuation and claims the benefit of priority of International Application No. PCT/US02/06962 filed Feb. 21, 2002, designating the United States of America and published in English, which claims the benefit of priority of U.S. Provisional Application No. 60/274,684 filed Mar. 9, 2001, both of which are hereby expressly incorporated by reference in their entireties.

SEQUENCE LISTING

The present application is being filed along with a Sequence Listing in electronic format. The Sequence Listing is provided as a file entitled NIH202-001C1C1_Sequence Listing.TXT, created Feb. 20, 2009, which is 7 Kb in size. The information in the electronic format of the Sequence Listing is incorporated herein by reference in its entirety.

FIELD OF THE INVENTION

The present invention discloses the construction of dengue virus subgenomic replicons containing large deletions in the structural region (C-preM-E) of the genome, which replicons are useful as vaccines to protect against dengue virus infection.

BACKGROUND OF THE INVENTION

The mosquito-borne flavivirus, dengue, is estimated to cause in each year 100 million cases of dengue fever (DF), 500,000 cases of dengue hemorrhagic fever (DHF) and 25,000 deaths, with 2.5 billion people at risk (Monath, T. P. 1994 *PNAS USA* 91:2395-2400). Although a successful vaccine against the prototypical flavivirus, yellow fever (YF) virus, has been in use since the 1930s and vaccines to two other flaviviruses, Japanese encephalitis (JE) virus and tick-borne encephalitis (TBE) virus are currently available, there is as yet no dengue vaccine approved for use (Cardosa, M. J. 1998 *Brit Med Bull* 54:395-405).

Dengue virus has a typical flavivirus genome structure, as described in FIG. 2A. The structural proteins, C, prM (M) and E, are involved in packaging, export and subsequent entry. The non-structural proteins, NS1, NS2A, NS2B, NS3, NS4A, NS4B and NS5 include an RNA-directed RNA polymerase, and a protease function involved in cleaving certain positions of the long viral polyprotein which contains all the viral genes (Chambers, T. J. et al. 1990 *Ann Rev Microbiol* 44:649-88; Rice, C. M. 1996 In: *Fields Virology*, 3rd ed. Philadelphia, Pa. Lippincott-Raven Publishers, p. 931-996).

The four serotypes of dengue virus ("1" through "4") share approximately 60%-74% amino acid residue identity with one another in the E gene (Thomas, C. J. et al. 1990 *Ann Rev Microbiol* 44:649-88) and induce cross-reacting antibodies (Heinz, F. X. 1986 *Adv Virus Res* 31:103-168). However, neutralizing antibodies to the structural proteins of one serotype of dengue typically not only fail to provide protection against other serotypes, but appear to cause the enhanced replication of virus seen in dengue hemorrhagic fever, which is generally seen upon reinfection by dengue virus of a different serotype. This antibody-dependent enhancement of infection (ADE), which is believed to be mediated by enhancement of viral uptake by macrophages (Morens, D. M. 1994 *Clin Infect Dis* 19:500-512) complicates dengue vaccine development, since an inadequate or modified immunogen may contribute to disease, rather than prevent infection (Halstead, S. B. 1988 *Science* 239:476-481).

Two strategies suggest themselves for circumventing the problems caused by cross reacting antibodies against the major structural proteins, prM and E. One strategy is to immunize with multiple strains of dengue virus to elicit high affinity, neutralizing antibodies against the multiple dengue serotypes. At least one vaccine to do this (using dengue vaccine candidates DEN-1 PDK13, DEN-2 PDK53, DEN-3 PGMK 30/F3, and DEN-4 PDK48) has been in clinical trials (Bhamarapravati, N. and Sutee, Y. 2000 *Vaccine* 18 Suppl 2:4447; Kanesa-thasan, N. et al. 2001 *Vaccine* 19:3179-3188). A second strategy is to induce immunity only to viral proteins other than prM and E. Several studies have shown that the nonstructural glycoprotein NS1 can play an important role in protection against dengue. Mice immunized with purified dengue-2 NS1 protein injected intramuscularly and boosted after 3 days and two weeks were protected from developing lethal dengue encephalitis upon subsequent challenge with dengue-2 virus (Schlesinger, J. J. et al. 1987 *J Gen Virol* 68:853-857). Similarly, mice immunized with recombinant vaccinia virus expressing authentic NS1 (Falgout, B. et al. 1990 *J Virol* 64:4356-4363) were protected against the development of dengue-4 virus encephalitis when challenged by intracerebral injection. Inoculation of mice with specific combinations of MAbs directed against dengue-2 NS1 (Henchal, E. A. et al. 1988 *J Gen Virol* 69:2101-2107) also protects against lethal virus encephalitis upon intracerebral dengue-2 challenge. Other nonstructural proteins are also immunogenic and may participate in eliciting protection (Brinton, M. A. et al. 1998 *Clin Diagn Virol* 10:129-39).

SEGUE TO SUMMARY OF THE INVENTION

Towards the goal of devising a "live" vaccine based on only non-structural dengue proteins, we have attempted to construct dengue virus genomes from which the pre-M and E genes have been deleted. Upon introduction into a host's cells, these sub-genomic fragments should replicate intracellularly and support prolonged expression of dengue non-structural proteins without producing the deleted structural proteins and without forming infectious virions. Sub-genomic replicons of several positive-strand RNA animal viruses have been reported, particularly yellow fever and Kunjin among the flaviviruses. These replicons, when introduced into host cells, replicate and make viral proteins for over 41 days (Khromykn, A. A. and Westaway, E. D. 1997 *J Virol* 71:1497-1505), but cannot form infectious virions because they lack critical structural proteins. Effectively delivered to host cells in vivo, such replicons should efficiently induce immunologic reactions against the expressed proteins remaining in the sub-genomic construct. Herein we describe the successful construction of two dengue virus sub-genomic constructs which replicate in LLC-MK2 cells in tissue culture when transfected in as full length RNA. We also report that expression of dengue virus proteins from these replicons can be supported by transfection of a DNA-based expression vector containing the replicon.

SUMMARY OF THE INVENTION

The present invention discloses the construction of dengue virus subgenomic replicons containing large deletions in the structural region (C-preM-E) of the genome, which replicons are useful as vaccines to protect against dengue virus infection.

BRIEF DESCRIPTION OF THE DRAWINGS

FIG. 1. Representation of ΔE, ΔME, and ΔCME dengue replicons. The ΔE replicon contains a deletion of the sequence coding for Envelope (E) protein. The ΔME replicon contains a deletion of the sequence coding for pre-Membrane (prM) and Envelope (E) proteins. The ΔCME contains a deletion of the sequence coding for Core (C), pre-Membrane (prM), and Envelope (E) proteins.

FIG. 3. Expression of dengue virus as determined by immunofluorescent staining with mouse anti-dengue virus-2. Cells were counterstained with Evans Blue, but different filtration systems available on the different microscopes variably blocked visualization of the background of cells fluorescing red. Transfection efficiencies were generally in the range of 0.01% to 1% and in the background of each photograph in this figure are numerous non-fluorescent cells, best visualized on an Apple Macintosh. In the experiments herein, cells were photographed variously with either 40× or 60× objectives. A, Dengue-2 wild type virus (48 hrs.); B, ΔprM-E (48 hrs.); C, ΔC-prM-E (48 hrs.); D, Dengue-2 wild type (8 days); E, ΔprM-E (8 days); F, ΔC-prM-E (8 days).

FIG. 6. Construction of wild type dengue virus and dengue virus replicon vectors used in these studies. The diagram at the top represents the wild type dengue virus genome.

DETAILED DESCRIPTION OF THE PREFERRED EMBODIMENT

Figure 2A:
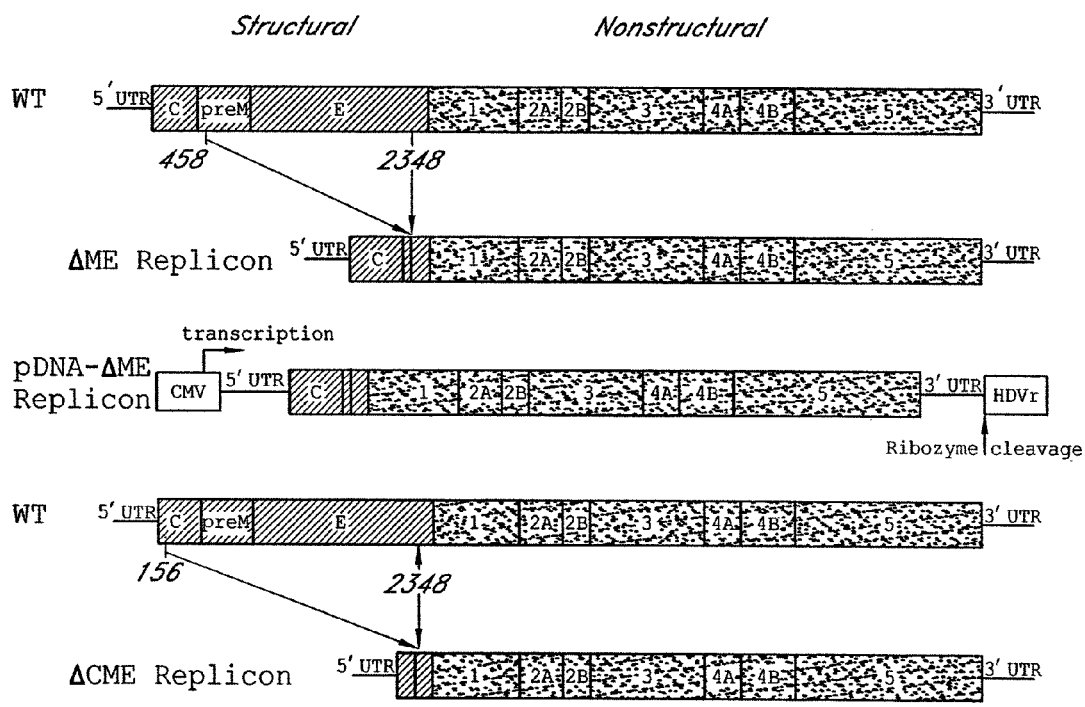
FIG. 2. A, Diagram of dengue virus genome and deletion mutations in this study. B, Sequences at the deletion points of mutants used in this study. ΔME Replicon: (AGTTGT, SEQ ID NO: 1; CGTAACAGCACC, SEQ ID NO: 2; GGTTCT, SEQ ID NO: 3); ΔCME Replicon (AGTTGT, SEQ ID NO: 4; GAGAGAAGCACC, SEQ ID NO: 5; GGTTCT, SEQ ID NO: 6).
Figure 2B:

The invention relates to a subgenomic replicon of dengue virus origin comprising a deletion for the sequence coding for C, PreM, and E structural proteins (ΔCME).

The invention also relates to a subgenomic replicon of dengue virus origin comprising a deletion for the sequence coding for PreM and E structural proteins (ΔME).

The invention also relates to a subgenomic replicon of dengue virus origin comprising a deletion for the sequence coding for E structural protein (ΔE).

The invention also relates to a subgenomic replicon of dengue virus type 1 origin comprising a deletion for the sequence coding for C, PreM, and E structural proteins (ΔCME).

The invention also relates to a subgenomic replicon of dengue virus type 1 origin comprising a deletion for the sequence coding for PreM and E structural proteins (ΔME).

The invention also relates to a subgenomic replicon of dengue virus type 1 origin comprising a deletion for the sequence coding for E structural protein (ΔE).

The invention also relates to a subgenomic replicon of dengue virus type 2 origin comprising a deletion for the sequence coding for C, PreM, and E structural proteins (ΔCME).

The invention also relates to a subgenomic replicon of dengue virus type 2 origin comprising a deletion for the sequence coding for PreM and E structural proteins (ΔME).

The invention also relates to a subgenomic replicon of dengue virus type 2 origin comprising a deletion for the sequence coding for E structural protein (ΔE).

The invention also relates to a subgenomic replicon of dengue virus type 3 origin comprising a deletion for the sequence coding for C, PreM, and E structural proteins (ΔCME).

The invention also relates to a subgenomic replicon of dengue virus type 3 origin comprising a deletion for the sequence coding for PreM and E structural proteins (ΔME).

The invention also relates to a subgenomic replicon of dengue virus type 3 origin comprising a deletion for the sequence coding for E structural protein (ΔE).

The invention also relates to a subgenomic replicon of dengue virus type 4 origin comprising a deletion for the sequence coding for C, PreM, and E structural proteins (ΔCME).

The invention also relates to a subgenomic replicon of dengue virus type 4 origin comprising a deletion for the sequence coding for PreM and E structural proteins (ΔME).

The invention also relates to a subgenomic replicon of dengue virus type 4 origin comprising a deletion for the sequence coding for E structural protein (ΔE).

The invention also relates to a subgenomic replicon of dengue virus origin comprising a deletion for the sequence coding for C, PreM, and E structural proteins (ΔCME), for PreM and E structural proteins (ΔME), or for E structural protein (ΔE); and further comprising part or all of the 5'UTR; at least about the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, or 175 nucleotides of C protein; at least about the last 1, 2, 3, 4, 5, 6, 7, 8, 9. 10, 11, 12, 13, 14, 15, 16, 17, 18. 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159. 160, 161, 162, 163, 164, 165, 166, 167, 168, 169, 170, 171, 172, 173, 174, or 175 nucleotides of E protein; substantially all of the nonstructural region; and part or all of the 3'UTR.

The invention also relates to a subgenomic replicon of dengue virus origin comprising a deletion for the sequence coding for C, PreM, and E structural proteins (ΔCME), for PreM and E structural proteins (ΔME), or for E structural protein (ΔE), which is adapted to receive at least a nucleotide sequence without disrupting its replication capabilities.

The invention also relates to a vaccine comprising a subgenomic replicon of dengue virus origin which comprises a deletion for the sequence coding for C, PreM, and E structural proteins (ΔCME), for PreM and E structural proteins (ΔME), or for E structural protein (ΔE), optionally which is adapted to receive at least a nucleotide sequence without disrupting its replication capabilities, and a pharmaceutically acceptable carrier.

The invention also relates to a therapeutic comprising a subgenomic replicon of dengue virus origin which comprises a deletion for the sequence coding for C, PreM, and E structural proteins (ΔCME), for PreM and E structural proteins (ΔME), or for E structural protein (ΔE), optionally which is adapted to receive at least a nucleotide sequence without disrupting its replication capabilities, and a pharmaceutically acceptable carrier.

The invention also relates to a dengue virus like particle comprising a subgenomic replicon of dengue virus origin which comprises a deletion for the sequence coding for C, PreM, and E structural proteins (ΔCME), for PreM and E structural proteins (ΔME), or for E structural protein (ΔE), optionally which is adapted to receive at least a nucleotide sequence without disrupting its replication capabilities, and structural proteins of the homologous dengue virus wherein said structural proteins encapsulate said subgenomic replicon.

The invention also relates to a method of immunization comprising administering to an individual in need thereof a subgenomic replicon of dengue virus origin which comprises a deletion for the sequence coding for C, PreM, and E structural proteins (ΔCME), for PreM and E structural proteins (ΔME), or for E structural protein (ΔE), optionally which is adapted to receive at least a nucleotide sequence without disrupting its replication capabilities.

The invention also relates to a method of immunization comprising administering to an individual in need thereof a dengue virus like particle which comprises a subgenomic replicon of dengue virus origin comprising a deletion for the sequence coding for C, PreM, and E structural proteins (ΔCME), for PreM and E structural proteins (ΔME), or for E structural protein (ΔE), optionally which is adapted to receive at least a nucleotide sequence without disrupting its replication capabilities, and structural proteins of the homologous dengue virus wherein said structural proteins encapsulate said subgenomic replicon.

The invention also relates to a method of treatment comprising administering to an individual in need thereof a subgenomic replicon of dengue virus origin which comprises a deletion for the sequence coding for C, PreM, and E structural proteins (ΔCME), for PreM and E structural proteins (ΔME), or for E structural protein (ΔE), optionally which is adapted to receive at least a nucleotide sequence without disrupting its replication capabilities.

The invention also relates to a method of treatment comprising administering to an individual in need thereof a dengue virus like particle which comprises a subgenomic replicon of dengue virus origin comprising a deletion for the sequence coding for C, PreM, and E structural proteins (ΔCME), for PreM and E structural proteins (ΔME), or for E structural protein (ΔE), optionally which is adapted to receive at least a nucleotide sequence without disrupting its replication capabilities, and structural proteins of the homologous dengue virus wherein said structural proteins encapsulate said subgenomic replicon.

Dengue Genome

Dengue viruses are part of the Flavivirus genus in the Flaviviridae family. Flaviviruses are single stranded RNA (ssRNA) positive strand viruses which do not have a DNA stage. The flavivirus genome is approximately 11 kb and consists of a long Open Reading Frame (ORF) flanked by a 5' Untranslated Region (UTR) (95-132 nt) and a 3'UTR (114-624 nt). The UTRs contain conserved RNA elements and play a role in viral RNA replication. The ORF contains three structural proteins, Core (C), pre-Membrane (prM), Envelope (E), and seven non-structural proteins, NS1, NS2A, NS2B, NS3, NS4A, NS4B, and NS5.

Subgenomic Replicons

Although the present invention describes a means for producing proteins, the term "protein" should be understood to include within its scope parts of proteins such as peptide and polypeptide sequences.

In use, the replicon is introduced into a host cell where gene expression and hence protein production take place. Because the vector is capable of self-replication, multiple copies of the replicon will also be generated. This leads to an exponential increase in the number of replicons in the host cell as well as an exponential increase in the amount of protein that is produced.

Optionally, upon introduction of a second vector, containing the structural genes necessary to produce virus particles, structural proteins are produced. These proteins encapsulate the replicon therein forming a "pseudo" recombinant virus that is capable of producing heterologous protein inside another cell. The pseudo-virus cannot, however, replicate to produce new viral particles because the genes necessary for the production of the structural proteins are not provided in the replicon. Pseudo-virus stock will only be produced when co-transfection of the replicon and the vector bearing the structural genes occurs.

It will be appreciated that any replicon derived from a dengue RNA, which is lacking at least a structural gene, and, optionally, which is adapted to receive at least a nucleotide sequence may be employed in the present invention. Preferably, the replicon is derived from dengue types 1, 2, 3, or 4 and is adapted to comprise (open language) or consist of (closed language) the following: part or all of the 5'UTR; at least about the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, or 175 nucleotides of C protein (preferably the first 20 to 60 nucleotides); at least about the last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, or 175 nucleotides of E protein (preferably the last 72 nucleotides); substantially all of the nonstructural region; and part or all of the 3'UTR. Replication of a flavivirus genome is dependent on the genes in the nonstructural region of the genome being present during transcription and translation. Preferably any modification made to the nonstructural region should not interfere with the functional activity of the genes within the nonstructural region of the genome.

Optimal dengue replicon design for transfection into eukaryotic cells might also include such sequences as: sequences to promote expression of the heterologous gene of interest, including appropriate transcription initiation, termination, and enhancer sequences; as well as sequences that enhance translation efficiency, such as the Kozak consensus sequence; and an internal ribosomal entry site (IRES) of picornaviruses.

Therefore, while the nucleotide sequence may be placed under the control of dengue regulatory machinery in the replicon, it may alternatively be controlled by one or more alternate regulatory elements capable of promoting expression. Such elements will be well known to those of ordinary skill in this field. In one embodiment of the invention the replicon contains a eucaryotic promoter sequence (such as a CMV promoter) upstream of the 5'UTR and a ribozyme sequence (such as a delta virus ribozyme) followed by a transcription terminator sequence downstream of the 3'UTR. Transfection of the resulting plasmid DNA in cells will ensure production of a dengue replicon RNA transcript with the authentic 5'-end by cellular RNA polymerase II and with the authentic 3'-end cleaved by delta virus ribozyme, which is preferred for its efficient replication.

It will be appreciated that the nucleotide sequence inserted into the replicon may encode part or all of any natural or recombinant protein except for the structural protein sequence into which or in place of which the nucleotide sequence is inserted. For example, the nucleotide sequence may encode a single polypeptide sequence or a plurality of sequences linked together in such a way that each of the sequences retains its identity when expressed as an amino acid sequence. Where the nucleotide sequence encodes a plurality of peptides, the peptides should be linked together in such a way that each retains its identity when expressed. Such polypeptides may be produced as a fusion protein or engineered in such a manner to result in separate polypeptide or peptide sequences.

Where the vector is used to deliver nucleotide sequences to a host cell to enable host cell expression of immunogenic polypeptides, the nucleotide sequence may encode one or more immunogenic polypeptides in association with a range of epitopes which contribute to T-cell activity. In such circumstances the heterologous nucleotide sequence preferably encodes epitopes capable of eliciting either a helper T-cell response or a cytotoxic T-cell (CTL) response or both.

The replicon described herein may also be engineered to express multiple nucleotide sequences allowing co-expression of several proteins such as a plurality of antigens together with cytokines or other immunomodulators to enhance the generation of an immune response. Such a replicon might be particularly useful for example in the production of various proteins at the same time or in gene therapy applications.

By way of example only the nucleotide sequence may encode the DNA sequence of one or more of the following: malarial surface antigens; betagalactosidase; green fluorescence protein; any major antigenic viral antigen, e.g., Haemagglutinin from influenza virus or a human immunodeficiency virus (HIV) protein such as HIV gp120 (or gp 160) and HIV gag protein or part thereof; any eukaryotic polypeptide such as, for example, a mammalian polypeptide such as an enzyme, e.g., chymosin or gastric lipase; an enzyme inhibitor, e.g., tissue inhibitor of metalloproteinase (TIMP); a hormone, e.g., growth hormone; a lymphokine, e.g., an interferon; a cytokine, e.g., an interleukin (e.g., IL-2, IL-4, IL-6 etc); a chemokine, e.g., macrophage inflammatory protein-2; a plasminogen activator, e.g., tissue plasminogen activator (tPA) or prourokinase; or a natural, modified or chimeric immunoglobulin or a fragment thereof including chimeric immunoglobulins having dual activity such as antibody enzyme or antibody-toxin chimeras.

To optimize expression of desired foreign proteins, an autocatalytic peptide cleavage site is added to the replicon. This construct will allow one to place an autocatalytic peptide cleavage site between two protein coding sequences. When the protein is expressed from the nucleic acid construct, the autocatalytic peptide cleavage site will automatically cleave the desired foreign protein.

The table below compares known autocatalytic peptide cleavage sites:

| | -16 -1 | 1 7 |
|---|---|---|
| Mengo virus, strain M | GYFSDLLIHDVETNPG (SEQ ID. NO.: 7) | PFTFKPRQ (SEQ ID. NO.: 8) |
| Encephalomyocarditis virus, strain B | GYFADLLIHDIETNPG (SEQ ID. NO.: 9) | PFMAKPKK (SEQ ID. NO.: 10) |

-continued

| | -16 | -1 1 | 7 |
|---|---|---|---|
| Encephalomyocarditis virus, strain Rueckert | GYFADLLIHDIETNPG (SEQ ID. NO.: 11) | PFMFRPRK (SEQ ID. NO.: 12) | |
| Theilers murine encephalomyelitis virus, strain Bean | DYYRQRLIHDVETNPG (SEQ ID. NO.: 13) | PVQSVFQP (SEQ ID. NO.: 14) | |
| Theilers murine encephalomyelitis virus, strain GDVII | DYYKQRLIHDVEMNPG (SEQ ID. NO.: 15) | PVQSVFQP (SEQ ID. NO.: 16) | |
| Foot-and-mouth disease virus, strain 01 Kaufbeuren | NFDLLKLAGDVESNPG (SEQ ID. NO.: 17) | PFFFSDVR (SEQ ID. NO.: 18) | |
| Bovine rotavirus type C | QIDRILISGDIELNGP (SEQ ID. NO.: 19) | PNALVKLN (SEQ ID. NO.: 20) | |
| Porcine rotavirus type C | QIDRILISGDVELNPG (SEQ ID. NO.: 21) | PDPLIRLN (SEQ ID. NO.: 22) | |

Preferably, the autocatalytic peptide cleavage site is at least 17 amino acids in length with 16 amino acids extending in the minus direction (NH2 direction) and one residue in the plus direction (COOH direction) relative to the cleavage site. Ryan and Drew, *EMBO J* 13: 928 (1994) added 3 amino acids (QLL) extending in the minus direction corresponding to the three C-terminal residues of capsid protein 1D apropos foot-and-mouth disease virus 2A oligopeptide to mediate cleavage of an artificial polyprotein. Other peptide cleavage sites, auto-catalytic or otherwise, are contemplated that act as a protease.

The second vector that contains the dengue structural gene(s) should be engineered to prevent recombination with the self-replicating expression vector. One means for achieving this end is to prepare the second vector from genetic material that is heterologous in origin to the origin of the self-replicating expression vector. For example, the second vector might be prepared from Semliki Forest virus (SFV) as the replicon is prepared from dengue virus.

To optimize expression of the dengue structural genes, the second vector might include such sequences as: sequences to promote expression of the genes of interest, including appropriate transcription initiation, termination, and enhancer sequences; as well as sequences that enhance translation efficiency, such as the Kozak consensus sequence. Preferably, the second vector contains separate regulatory elements associated with each of the different structural genes expressed by the vector. Most preferably, the dengue C gene and the prME genes are placed under the control of separate regulatory elements in the vector.

The present invention also provides stable cell lines capable of persistently producing replicon RNAs. To prepare such cell lines, the described vectors are constructed in selectable form by inserting an IRES-Neo (neomycin transferase) or such cassette into the 3'UTR, the 5'UTR, in place of a structural gene, or other.

Host cell lines contemplated to be useful in the method of the invention include any eukaryotic cell lines that can be immortalized, i.e., are viable for multiple passages, (e.g., greater than 50 generations), without significant reduction in growth rate or protein production. Useful cell lines should also be easy to transfect, be capable of stably maintaining foreign RNA with an unarranged sequence, and have the necessary cellular components for efficient transcription, translation, post-translation modification, and secretion of the protein. Currently preferred cells are those having simple media component requirements, and which can be adapted for suspension culturing. Most preferred are mammalian cell lines that can be adapted to growth in low serum or serum-free medium. Representative host cell lines include BHK (baby hamster kidney), VERO, C6-36, COS, CHO (Chinese hamster ovary), myeloma, HeLa, fibroblast, embryonic and various tissue cells, e.g., kidney, liver, lung and the like. Desirably a cell line is selected from one of the following: BHK21 (hamster), SK6 (swine), VERO (monkey), L292 (mouse), HeLa (human), HEK (human), 2fTGH cells, HepG2 (human). Useful cells can be obtained from the American Type Culture Collection (ATCC), Manassas, Va.

With respect to the transfection process used in the practice of the invention, all means for introducing nucleic acids into a cell are contemplated including, without limitation, $CaPO_4$ co-precipitation, electroporation, DEAE-dextran mediated uptake, protoplast fusion, microinjection and lipofusion. Moreover, the invention contemplates either simultaneous or sequential transfection of the host cell with vectors containing the gene sequences. In one preferred embodiment, host cells are sequentially transfected with at least two unlinked vectors, one of which contains dengue replicon expressing heterologous gene, and the other of which contains the structural genes.

The present invention also provides virus like particles containing dengue replicons and a method for producing such particles. It will be appreciated by those skilled in the art that virus like particles that contain dengue derived replicons can be used to deliver any nucleotide sequence to a cell. Further, the replicons may be of either DNA or RNA in structure. One particular use for such particles is to deliver nucleotide sequences coding for polypeptides that stimulate an immune response. Such particles may be employed as a therapeutic or in circumstances where the nucleotide sequence encodes peptides that are capable of eliciting a protective immune response so that they may be used as a vaccine. Another use for such particles is to introduce into a subject a nucleotide sequence coding for a protein that is either deficient or is being produced in insufficient amounts in a cell.

The replicon containing dengue virus like particles that contain nucleotide coding sequence for immunogenic polypeptide(s) as active ingredients may be prepared as injectables, either as liquid solutions or suspensions; solid forms suitable for solution in, or suspension in, liquid prior to injection may also be prepared. The dengue replicon therapeutic(s) may also be mixed with excipients that are pharmaceutically acceptable and compatible with the replicon encapsulated viral particle. Suitable excipients are, for example, water, saline, dextrose, glycerol, ethanol, or the like and combinations thereof. In addition, if desired, the therapeutic may contain minor amounts of auxiliary substances such as wetting or emulsifying agents, pH buffering agents, and/or adjuvant which enhance the effectiveness of the therapeutic.

The replicon containing dengue virus like particles may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of virus like particles, preferably 25-70%.

The dengue virus like particles may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamins, trimethylamine, 2-ethylamino ethanol, histidino, procaine, and the like.

The dengue virus like particles may be administered in a manner compatible with the dosage formulation and in such amount as will be prophylactically and/or therapeutically effective. The dose of viral particles to be administered depends on the subject to be treated, the type of nucleotide sequence that is being administered and the type of expression efficiency of that sequence and in the case where the nucleotide sequence encodes immunogenic peptide/polypeptides the degree of protection desired. Precise amounts of active ingredient required to be administered may depend on the judgment of the practitioner and may be peculiar to each subject.

The dengue virus like particles may be given to a subject in a single delivery schedule, or preferably in a multiple delivery schedule. A multiple delivery schedule is one in which a primary course of delivery may be with 1-10 separate doses, followed by other doses given at subsequent time intervals required to maintain and or re-enforce the effect sought and if needed, a subsequent dose(s) after several months. The delivery regimen will also, at least in part, be determined by the need of the individual and be dependent upon the judgment of the practitioner.

Genetic Immunization and Gene Therapy

In some embodiments, the present invention relates to genetic methods of eliciting immune responses in an individual which can protect an individual from dengue infection or combat dengue diseases. According to the present invention, genetic material that encodes a subgenomic replicon is directly administered to an individual either in vivo or to the cells of an individual ex vivo. The genetic material encodes a peptide or protein that shares at least an epitope with a dengue nonstructural protein to be targeted. The genetic material is expressed by the individual's cells to form immunogenic target proteins that elicit an immune response. The resulting immune response is broad based: in addition to a humoral immune response, both arms of the cellular immune response are elicited. Thus, the immune responses elicited by vaccination methods of the present invention are particularly effective to protect against dengue infection or combat diseases associated with dengue.

The immune response elicited by the target protein that is produced by vaccinated cells in an individual is a broad-based immune response which involves B cell and T cell responses including cytotoxic T cell (CTL) responses. The target antigens produced within the cells of the host are processed intracellularly: broken down into small peptides, bound by Class I MHC molecules, and expressed on the cell surface. The Class I MHC-target antigen complexes are capable of stimulating CD8+ T-cells, which are phenotypically the killer/suppressor cells. Genetic immunization according to the present invention is thus capable of eliciting cytotoxic T-cell (CTL) responses (killer cell responses). It has been observed that genetic immunization according to the present invention is more likely to elicit CTL responses than other methods of immunization.

Genetic immunization according to the present invention elicits an effective immune response without the use of infective agents or infective vectors. Vaccination techniques which usually do produce a CTL response do so through the use of an infective agent. A complete, broad based immune response is not generally exhibited in individuals immunized with killed, inactivated or subunit vaccines. The present invention achieves the full complement of immune responses in a safe manner without the risks and problems associated with vaccinations that use infectious agents.

According to some embodiments of the present invention, cells are treated with compounds that facilitate uptake of genetic constructs by the cells. According to some embodiments of the present invention, cells are treated with compounds that stimulate cell division and facilitate uptake of genetic constructs. Administration of compounds that facilitate uptake of genetic constructs by the cells including cell stimulating compounds results in a more effective immune response against the target protein encoded by the genetic construct.

According to some embodiments of the present invention, the genetic construct is administered to an individual using a needleless injection device. According to some embodiments of the present invention, the genetic construct is simultaneously administered to an individual intradermally, subcutaneously and intramuscularly using a needleless injection device. Administration of genetic constructs using needleless injection devices is disclosed in the art.

According to the present invention, DNA or RNA that encodes a target protein is introduced into the cells of an individual where it is expressed, thus producing the target protein. The DNA or RNA is linked to regulatory elements necessary for expression in the cells of the individual. Regulatory elements for DNA include a promoter and a polyadenylation signal. In addition, other elements, such as a Kozak region, may also be included in the genetic construct.

The genetic construct of a genetic vaccine comprises a nucleotide sequence that encodes a target protein operably linked to regulatory elements needed for gene expression. Accordingly, incorporation of the DNA or RNA molecule into a living cell results in the expression of the DNA or RNA encoding the target protein and thus, production of the target protein.

When taken up by a cell, the genetic construct which includes the nucleotide sequence encoding the target protein operably linked to the regulatory elements may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Since integration into the chromosomal DNA necessarily requires manipulation of the chromosome, it is preferred to maintain the DNA construct as a replicating or non-replicating extra-chromosomal molecule. This reduces the risk of damaging the cell by splicing into the chromosome without affecting the effectiveness of the vaccine. Alternatively, RNA may be administered to the cell. It is also contemplated to provide the genetic construct as a linear minichromosome including a centromere, telomeres and an origin of replication.

The necessary elements of a genetic construct of a genetic vaccine include a nucleotide sequence that encodes a target protein and the regulatory elements necessary for expression of that sequence in the cells of the vaccinated individual. The regulatory elements are operably linked to the DNA sequence that encodes the target protein to enable expression.

The molecule that encodes a target protein is a protein-encoding molecule which is translated into protein. Such molecules include DNA or RNA which comprise a nucleotide sequence that encodes the target protein. These molecules may be cDNA, genomic DNA, synthesized DNA or a hybrid thereof or an RNA molecule such as mRNA. Accordingly, as used herein, the terms "genetic construct" and "nucleotide sequence" are meant to refer to both DNA and RNA molecules.

The regulatory elements necessary for gene expression of a DNA molecule include: a promoter, an initiation codon, a stop codon, and a polyadenylation signal. In addition, enhancers are often required for gene expression. It is necessary that these elements be operable in the vaccinated individual. Moreover, it is necessary that these elements be operably linked to the nucleotide sequence that encodes the target protein such that the nucleotide sequence can be expressed in the cells of a vaccinated individual and thus the target protein can be produced.

Initiation codons and stop codon are generally considered to be part of a nucleotide sequence that encodes the target protein. However, it is necessary that these elements are functional in the vaccinated individual.

Similarly, promoters and polyadenylation signals used must be functional within the cells of the vaccinated individual.

In order to be a functional genetic construct, the regulatory elements must be operably linked to the nucleotide sequence that encodes the target protein. Accordingly, it is necessary for the initiation and termination codons to be in frame with the coding sequence.

In order to maximize protein production, regulatory sequences may be selected which are well suited for gene expression in the vaccinated cells. Moreover, codons may be selected which are most efficiently transcribed in the vaccinated cell. One having ordinary skill in the art can produce DNA constructs which are functional in vaccinated cells.

In order to test expression, genetic constructs can be tested for expression levels in vitro using tissue culture of cells of the same type as those to be vaccinated. For example, if the genetic vaccine is to be administered into human muscle cells, muscle cells grown in culture such as solid muscle tumors cells of rhabdomyosarcoma may be used as an in vitro model to measure expression level.

According to the invention, the genetic vaccine may be administered directly into the individual to be immunized or ex vivo into removed cells of the individual which are reimplanted after administration. By either route, the genetic material is introduced into cells which are present in the body of the individual. Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection. Genetic constructs may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the genetic construct is taken up by the cells, they are reimplanted into the individual. It is contemplated that otherwise non-immunogenic cells that have genetic constructs incorporated therein can be implanted into the individual even if the vaccinated cells were originally taken from another individual.

The genetic vaccines according to the present invention comprise about 1 nanogram to about 1000 micrograms of DNA. In some preferred embodiments, the vaccines contain about 10 nanograms to about 800 micrograms of DNA. In some preferred embodiments, the vaccines contain about 0.1 to about 500 micrograms of DNA. In some preferred embodiments, the vaccines contain about 1 to about 350 micrograms of DNA. In some preferred embodiments, the vaccines contain about 25 to about 250 micrograms of DNA. In some preferred embodiments, the vaccines contain about 100 micrograms DNA.

The genetic vaccines according to the present invention are formulated according to the mode of administration to be used. One having ordinary skill in the art can readily formulate a genetic vaccine that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vaso-constriction agent is added to the formulation. The pharmaceutical preparations according to the present invention are provided sterile and pyrogen free.

Genetic constructs may optionally be formulated with one or more response enhancing agents such as: compounds which enhance transfection, i.e., transfecting agents; compounds which stimulate cell division, i.e., replication agents; compounds which stimulate immune cell migration to the site of administration, i.e., inflammatory agents; compounds which enhance an immune response, i.e., adjuvants or compounds having two or more of these activities.

In a preferred embodiment, bupivacaine, a well known and commercially available pharmaceutical compound, is administered prior to, simultaneously with or subsequent to the genetic construct. Bupivacaine and the genetic construct may be formulated in the same composition. Bupivacaine is particularly useful as a cell stimulating agent in view of its many properties and activities when administered to tissue. Bupivacaine promotes and facilitates the uptake of genetic material by the cell. As such, it is a transfecting agent. Administration of genetic constructs in conjunction with bupivacaine facilitates entry of the genetic constructs into cells. Bupivacaine is believed to disrupt or otherwise render the cell membrane more permeable. Cell division and replication is stimulated by bupivacaine. Accordingly, bupivacaine acts as a replicating agent. Administration of bupivacaine also irritates and damages the tissue. As such, it acts as an inflammatory agent which elicits migration and chemotaxis of immune cells to the site of administration. In addition to the cells normally present at the site of administration, the cells of the immune system which migrate to the site in response to the inflammatory agent can come into contact with the administered genetic material and the bupivacaine. Bupivacaine, acting as a transfection agent, is available to promote uptake of genetic material by such cells of the immune system as well.

Bupivacaine is related chemically and pharmacologically to the aminoacyl local anesthetics. It is a homologue of mepivacaine and related to lidocaine. Bupivacaine renders muscle tissue voltage sensitive to sodium challenge and effects ion concentration within the cells. A complete description of bupivacaine's pharmacological activities can be found in Ritchie, J. M. and N. M. Greene, The Pharmacological Basis of Therapeutics, Eds.: Gilman, A. G. et al, 8th Edition, Chapter 15:3111. Bupivacaine and compounds that display a functional similarity to bupivacaine are preferred in the method of the present invention.

Bupivacaine-HCl is chemically designated as 2-piperidinecarboxamide, 1-butyl-N-(2,6-dimethylphenyl)monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). Bupivacaine is commercially formulated with and without methylparaben and with or without epinephrine. Any such formulation may be used. It is commercially available for pharmaceutical use in concentration of 0.25%, 0.5% and 0.75% which may be used on the invention. Alternative concentrations which elicit desirable effects may be prepared if desired.

Other contemplated response enhancing agents which may function transfecting agents and/or replicating agents and/or inflammatory agents and which may be co-adminstered with bupivacaine and similar acting compounds include lectins, growth factors, cytokines and lymphokines such as alpha-interferon, gamma-interferon, platelet derived growth factor (PDGF), gCSF, gMCSF, TNF, epidermal growth factor (EGF), IL-1, IL-2, IL-4, IL-6, IL-8, IL-10 and IL-12 as well as collagenase, fibroblast growth factor, estrogen, dexamethasone, saponins, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalane, hyaluronic acid and hyaluronidase may also be used administered in conjunction with the genetic construct. In some embodiments, combinations of these agents are administered in conjunction with bupivicaine and the genetic construct. For example, bupivacaine and either hyaluronic acid or hyaluronidase are co-administered with a genetic construct.

In some embodiments of the invention, the genetic construct is injected with a needleless injection device. The needleless injection devices are particularly useful for simultaneous administration of the material intramuscularly, intradermally and subcutaneously.

In some embodiments of the invention, the genetic construct is administered with a response enhancing agent by means of a microprojectile particle bombardment procedure as taught by Sanford et al. in U.S. Pat. No. 4,945,050 issued Jul. 31, 1990.

In some embodiments of the invention, the genetic construct is administered as part of a liposome complex with a response enhancing agent.

In some embodiments of the invention, the individual is subject to a single vaccination to produce a full, broad immune response. In some embodiments of the invention, the individual is subject to a series of vaccinations to produce a full, broad immune response. According to some embodiments of the invention, at least two and preferably four to five injections are given over a period of time. The period of time between injections may include from 24 hours apart to two weeks or longer between injections, preferably one week apart. Alternatively, at least two and up to four separate injections are given simultaneously at different sites.

While this disclosure generally discusses immunization in the context of prophylactic methods of protection, the term "immunizing" is meant to refer to both prophylactic and therapeutic methods. Thus, a method of immunizing includes both methods of protecting an individual from dengue challenge as well as methods of treating an individual suffering from dengue disease. Accordingly, the present invention may be used as a vaccine for prophylactic protection or in a therapeutic manner; that is, as immunotherapeutic methods and preparations.

Other aspects of the invention include the use of genetic constructs in methods of introducing therapeutic genes into cells of an individual. Thus, one aspect of the present invention relates to gene therapy; that is, to methods of introducing nucleic acid molecules that encode therapeutic proteins into the cells of an individual. The administration protocols and genetic constructs useful in gene therapy applications are the same as those described above for genetic immunization except the genetic constructs include nucleotide sequences that encode proteins whose presence in the individual will eliminate a deficiency in the individual and/or whose presence will provide a therapeutic effect on the individual.

Construction of Dengue Replicons and Optional Encapsidation

Nucleotide sequences encoding the structural and non-structural proteins of all four dengue types have been reported. Type I: Fu et al. 1992 *Virology* 188:953; Type II: Gualano et al. 1998 *J Gen Virology* 79:437; Type III: Osatomi et al. 1990 *Virology* 176:643; Type IV: Zhao et al. 1986 *Virology* 155:77; Mackow et al. 1987 *Virology* 159:217.

Several dengue subgenomic replicons containing large deletions in the structural region (C-prM-E) can be constructed. Referring to FIG. 1, representative are ΔE, ΔME, and ΔCME dengue replicons. The ΔE replicon contains a deletion of the sequence coding for Envelope (E) protein. The ΔME replicon contains a deletion of the sequence coding for pre-Membrane (prM) and Envelope (E) proteins. The ΔCME contains a deletion of the sequence coding for Core (C), pre-Membrane (prM), and Envelope (E) proteins.

All deletion constructs may be prepared from cDNA clones used in the construction of plasmid dengue for generation of infectious dengue RNA by PCR-directed technology, using appropriate primers and conventional cloning. ΔC, ΔME, and ΔCME, and derivatives, are prepared to comprise (open language) or consist of (closed language) the following: part or all of the 5'UTR; at least about the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, or 175 nucleotides of C protein; at least about the last 1, 2, 3, 4, 5, 6, 7, 8, 9. 10, 11, 12, 13, 14, 15, 16, 17, 18. 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159. 160, 161, 162, 163, 164, 165, 166, 167, 168, 169, 170, 171, 172, 173, 174, or 175 nucleotides of E protein; substantially all of the nonstructural region; and part or all of the 3'UTR.

Evidence of replication of these RNAs after introduction into host cells is sought by immunofluorescence analysis of cells with antibodies to dengue proteins or by radioimmunoprecipitation analysis of lysates with antibodies to dengue proteins. No apparent cytopathic effect is observed in the great majority of the antibody positive cells at any time post-transfection. Reverse transcription PCR and Northern blot analysis confirm accumulation of dengue-specific RNA in cells transfected with ΔC, ΔME, and ΔCME, and derivatives.

A minimal sequence in core protein, or envelope protein, required for RNA replication is defined. Replicon constructs containing sequences coding for only the first amino acids of core protein, or only the last amino acids of envelope protein, are prepared. Deletions in the C coding sequence, or E coding sequence, are monitored for translation efficiency and replication activity. Translation efficiency may be unaffected. Replication activity is compared. Immunofluorescence results and Northern blot analysis may identify the minimal sequence required for RNA replication.

The effect of deletions in the 5'UTR and 3'UTR on RNA replication is determined. Replicon constructs with deletions in the 5'UTR or 3'UTR are prepared. Immunofluorescence results and Northern blot analysis may identify the 5'UTR and 3'UTR sequence(s) that may be removed without deleterious effect on RNA replication.

Multi-cistronic dengue replicon RNAs expressing heterologous genes are prepared. As a first step, an expression cassette is prepared for insertion into the 3'UTR, the 5'UTR, in place of a structural gene, or other. Initially, the IRES from EMCV is linked to a reporter gene to create an IRES-reporter gene cassette. The IRES from EMCV ensures cap-independent internal initiation of translation of the reporter gene to which it is linked. For example, an IRES-CAT gene cassette is cloned. The expression cassette is inserted in the plus orientation. Synthesis of plus strands of replicon RNA during replication is monitored via expression of the CAT gene.

To select for cells persistently expressing dengue replicons, the CAT gene is replaced by the Neo gene. The low percentage of replicon-expressing cells is strikingly enriched by selection during growth in the presence of the antibiotic G418. No apparent changes in the morphology of surviving positive cells is observed.

Dengue virus replicon RNA is encapsidated by a procedure involving two simultaneous or consecutive introductions into host cells, first with dengue virus replicon ΔC, ΔME, or ΔCME RNA, and about 24-hours later with a recombinant Semliki Forest virus (SFV) replicon RNA(s) expressing dengue virus structural proteins. The presence of dengue virus replicon RNA in encapsidated particles is demonstrated by its amplification and expression in host cells, detected by Northern blotting with dengue-specific probes and by immunofluorescence analysis with antibodies to dengue proteins. Infectious particles are pelleted by ultracentrifugation of the culture fluid from cells into which are introduced dengue virus replicon ΔC, ΔME, or ΔCME RNA, and recombinant Semliki Forest virus (SFV) replicon RNA(s) expressing dengue virus structural proteins. The particles are neutralized by preincubation with antibodies to dengue E protein. Radioimmunoprecipitation analysis with anti-E antibodies of the culture fluid of the doubly transfected cells shows the presence of C, preM, and E proteins in the immunoprecipitated particles. Reverse transcription PCR shows that the immunoprecipitated particles also contain dengue specific RNA. The encapsidated replicon particles sediment about the same as dengue virions in a 5 to 25% sucrose density gradient and are uniformly spherical, with a diameter that compares favorably with an approximately 50 nm diameter for dengue virions.

Example 1

As part of a program to develop a dengue virus vaccine which avoids the deleterious effects of antibody dependent enhancement (ADE) of infection mediated by antibodies to dengue virus structural proteins, we investigated the possibility of designing dengue vaccines based on non-structural proteins.

Our results indicate that dengue constructs which lack major structural proteins replicate intracellularly in tissue culture. These replicons are capable of prolonged expression of dengue virus non-structural proteins for at least seven days in culture.

Our conclusions indicate that dengue virus genomes lacking major structural proteins can, like other flaviviruses, replicate intracellularly and express virus non-structural proteins with minimal toxicity to host cells. These findings pave the way for the development of dengue virus replicons as a form of live, attenuated virus vaccine.

Development of Dengue Virus Type 2 Replicons Capable of Prolonged Expression in Host Cells Immunofluorescent analysis of cell cultures 48 hrs. post transfection demonstrates efficient expression of dengue virus proteins from wild type dengue virus as well as from both the ΔprM-E and ΔC-prM-E mutants (see FIG. 2 and FIGS. 3A, 3B and 3C). By this time point, the wild type virus has had a limited opportunity to be transmitted in secondary rounds of infection. Interestingly, pairs of fluorescent cells were often seen, suggesting cells continued to replicate after being successfully transfected by replication competent dengue replicons. This is particularly evident in FIGS. 3B and 3C.

By 8 days post transfection, wild type dengue virus expression is more widespread throughout the culture than it was 48 hrs. post transfection, presumably because it was able to undergo multiple rounds of replication and transmission (FIG. 3D). Cell cultures transfected with ΔprM-E (FIG. 3E) or ΔC-prM-E (FIG. 3F) still have cells efficiently expressing dengue proteins at 8 days, but they are more rare than they were at 48 hrs. post transfection. This is consistent with the inability of these mutants to make infectious virions and suggests that the viral proteins remaining in the dengue replicons may moderately retard cell growth and replication. However, in the experiments presented herein, cells were trypsinized and replated on day 7 post transfection, so they may not have had sufficient time to recover and replicate prior to harvest for immunofluorescence on day 8.

No fluorescent cells were ever seen at either 48 hrs. or 8 days post transfection with dengue deletion mutant ΔE, from which most of the E gene has been deleted. However, negative results are hard to interpret in this system.

Figure 4:
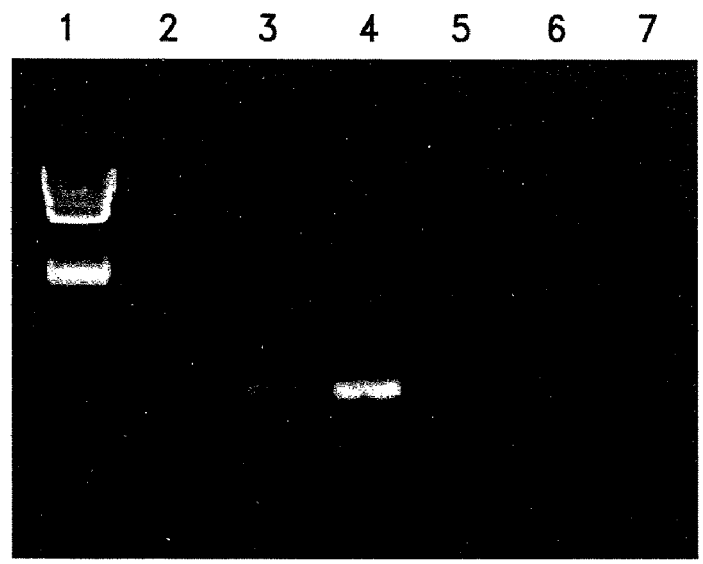
FIG. 4. Dengue virus RNA in transfected cells as determined by RT-PCR, normalized to total RNA: Lane 1, λ HindIll molecular weight markers; Lanes 2-4, ΔprM-E; 5-7, ΔE; 2 and 5, 6 hrs.; 3 and 6, 24 hrs.; 4 and 7, 48 hrs.

The prolonged expression of dengue virus proteins by the ΔprM-E and ΔC-prM-E replicons presumably is dependent on the ability of these sub-genomic fragments to replicate. Consistent with this presumption, ΔprM-E RNA was seen to sequentially increase in cultures over at least the first 48 hrs. post transfection (FIG. 4), whereas no dengue virus RNA was seen over this time period after transfection with ΔE RNA. RNA from both of these constructs is undetectable at 6 hrs. post transfection, suggesting that most of the transfecting RNA is rapidly degraded.

Figure 5:
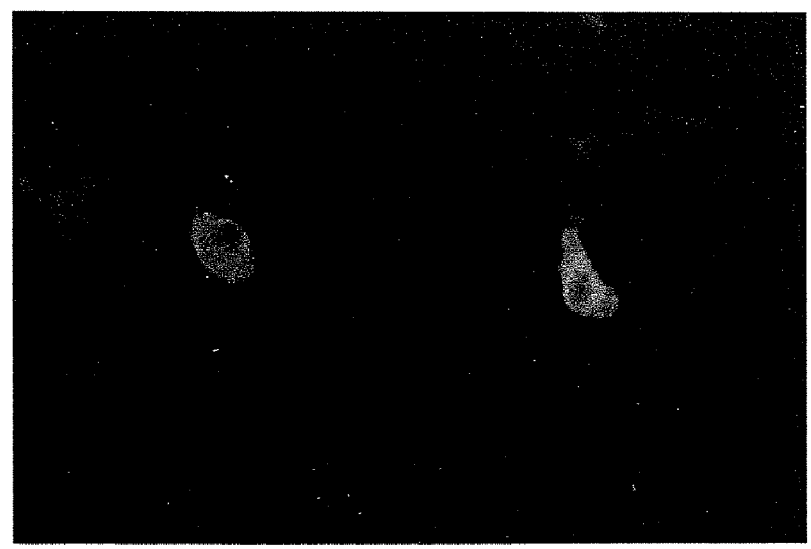
FIG. 5. Expression of dengue virus proteins by DNA-ΔprM-E transfected into cells in the form of plasmid DNA.

When the Δ-prM-E replicon is placed under the control of a cytomegalovirus (CMVB) promoter, it is still capable of active dengue virus protein expression when transfected into cells in the form of plasmid DNA (see FIG. 5).

The expression of dengue virus RNA and proteins in cultures transfected with the Δ-prM-E and ΔC-prM-E mutants is consistent with replication of the viral sub-genomes in these host cells. This is consistent with similar replicons constructed from Kunjin virus (Khromykn, A. A. and Westaway, E. D. 1997 *J Virol* 71:1497-1505). Most encouraging, however, is the finding of viral protein expression at long time points (8 days) subsequent to transfection with the ΔprM-E and ΔC-prM-E replicons in the absence of selection. Previous experiments with other flavivirus replicons have demonstrated expression for as long as 41 days post transfection (Khromykn, A. A. and Westaway, E. D. 1997 *J Virol* 71:1497-1505), but these replicons expressed neomycin and were grown under selective pressure. The longest, previously reported time for pure replicon expression in the absence of selection was just 72 hours (Khromykn, A. A. and Westaway, E. D. 1997 *J Virol* 71:1497-1505). We have not yet searched for continued expression beyond 8 days post transfection, but we have no reason to believe that is not readily achievable.

In order for the dengue replicons reported herein to be of immunologic value, they need to be expressible in a convenient form and (we anticipate) they need to produce NS1 protein. Formally, the data presented herein do not directly prove NS1 production, because the antisera used detect multiple viral structural and nonstructural proteins. Attempts to visualize dengue replicon protein synthesis by Western blotting were unsuccessful in our hands, presumably because of the comparatively low transfection efficiencies achieved. However, the previously demonstrated dependence of dengue virus replication on NS1 production (Lindenbach, B. D. and Rice, C. M. 1997 *J Virol* 71:9608-9617) and the fact that dengue virus RNA levels increase with time after transfection in the cultures used herein (implying active dengue RNA replication) together strongly imply the production of significant quantities of NS1 protein by these replicons. As for a suitable form of delivery, the ability of pDNA-ΔprM-E to make high levels of dengue proteins after transfection into cells in the form of DNA suggests the possibility of using DNA transfection to achieve immunization (Beard, C. et al. 1999 *J Biot* 73:243-249).

In conclusion, we have demonstrated the prolonged expression of dengue virus proteins from sub-genomic dengue RNA fragments, lacking major structural genes, transfected into tissue culture cells. This prolonged expression is associated with detectable increases in dengue RNA in the transfected tissue cultures, implying that the sub-genomic fragments are replicating, and implying the synthesis of NS1 protein and other viral non-structural proteins known to be required for viral genomic replication. The ability to express these sub-genomic dengue replicons from transfected DNA offers the possibility of using DNA-based, dengue replicon vaccines. Other delivery methods are contemplated, including the development of packaging cell lines.

Culturing of Dengue Virus

Dengue virus strains DEN1/WP and DEN2/NGC, kindly provided by Dr. Lewis Markoff (Polo, S. et al. 1997 *J Virol* 71:536-674; Pur, B. et al. 2000 *Virus Genes* 20:57-63), were passaged in monkey LLC-MK2 cells at 37° C. in a humidified incubator under 5% $CO_2$, using Medium 199 plus 10% fetal bovine serum (FBS) and 50 µg of Gentamicin per ml. The cells were trypsinized a day before virus infection and plated to reach approximately 80% confluence on the day of infection. Infections were typically at an MOI of 0.01 PFU/cell in Medium 199 plus 2% FBS.

In Vitro Mutagenesis

DNA fragments used for spanning the desired deletions (see FIG. 2) were synthesized by polymerase chain reaction (PCR) from two short overlapping primers. For the ΔCME replicon, the 5' primer was 5' ATCATTATGCTGATTCCAA-CAGTGATGGCG TTCCATTTAACCACACGTAACAG-CACCTCACTGTCTGTG3' (SEQ ID NO:23). For the ΔprME replicon, the 5' primer was 5'ACAGCTGTCGCTC-CTTCAATGACAATGC GTTGCATAGGAATAT-CAAATAGAAGCACCTCACTGTCTGTG3' (SEQ ID. NO.: 24). For both mutants, the 3' primer was 5'ATACAGCGT-CACGACTCCCACCAATACTAGT GACACAGACAGT-GAGGTGCT3' (SEQ ID. NO.: 25).

PDNA-ΔprM-E was constructed by placing the ΔprM-E replicon RNA under the transcriptional control of a CMV promoter and placing it upstream of a Hepatitis Delta Virus (HDV) self cleaving ribozyme.

Dengue-2 virus cDNA cloned in the yeast shuttle vector pBR424, linearized by excision of a short BamHI fragment was transfected into competent (Spencer, F. et al. 1993 *Methods Companion Methods Enzymol* 5:161-175) *S. cerevisiae* YPH857, kindly provided by Barry Falgout (CBER/FDA), along with the appropriate PCR fragment spanning the desired deletion. Yeast colonies which grew on tryptophan minus plates represented vectors which had recircularized by homologous recombination with these PCR fragments (Spencer, F. et al. 1993 *Methods Companion Methods Enzymol* 5:161-175). DNA from these colonies was transformed into *E. coli* Stbl 2 cells (Life Technologies, Inc.) to make sufficient quantities of dengue recombinant, genomic-length DNAs for characterization and analysis.

Expression of Virus and Replicons in Cells

The full length virus and replicon cDNA plasmids isolated from Stbl 2 cells were linearized with SacI, purified by Qiagen chromatography, and eluted by RNase-free water in preparation for transcription. The transcription reaction mixtures contained 1 µg of linearized DNA; 0.5 mM (each) ATP, CTP, and UTP; 0.1 mM GTP; 0.5 mM cap analog (NEBL); 10 mM DTT; 40 U of RNasin (Promega); 30 U of SP6 RNA polymerase; and 1×SP6 RNA polymerase buffer (Promega) in a volume of 30 µl. The reaction mixtures were incubated at 40° C. for 2 hrs. Aliquots (12.5 µl) of the reaction mixtures, containing full length viral RNA, were used to transfect approximately 2×10⁶ monkey LLC-MK2 cells in phosphate-buffered saline (PBS) by electroporation in a 0.4 cm gap electroporation cuvette. Each cuvette was pulsed at 200 V, 950 µF using a BioRad Genepuls electroporator. The cells were then resuspended in growth medium and plated on the appropriate tissue culture dish. Plasmid DNA-ΔprM-E was transfected into cells by electroporation using identical conditions.

After electroporation, cells were either plated directly on multiwell plates for harvest at short time periods (typically 48 hrs. or less) or on tissue culture dishes for trypsinization and seeding onto multiwell plates on the day before final harvest for longer time periods (typically 8 days post transfection).

Immuno-Histochemical Methods

Cells growing on chamber slides were rinsed in room-temperature PBS and then fixed in cold acetone for 10 min at −20° C. After being air dried, each chamber was covered with 50 µl of a 1:50 dilution of DEN2-specific hyperimmune mouse ascitic fluid (HMAF, American Type Culture Collection) in PBS plus 2% normal goat serum. Samples were incubated at room temperature for 1 h in a humidified atmosphere and then rinsed twice in PBS. Samples were similarly incubated with a 1:100 dilution of fluorescein isothiocyanate-labeled goat anti-mouse antibodies (Life Technologies) and rinsed twice in PBS. Cells in some experiments were counterstained with 0.02% Evans Blue.

Example 2

Despite tremendous progress in developing anti-retroviral drugs to combat HIV, there remains a need for an effective HIV vaccine. This need is particularly pressing in third world countries, where demographics and economics make drug therapy difficult to deliver. Although HIV infection elicits neutralizing antibodies and a cellular immune response against the virus (reviewed in Nathanson, N. and Mathieson, B. J. 2000 *J Infect Dis* 182:579-589; and Cho, M. W. 2000 *Adv Pharmacol* 49:263-314) and there exist "exposed uninfected" (EU) individuals that appear to have acquired resistance to infection by HIV (Clerici, M. et al. 1992 *J Infect Dis* 165: 1012-1019; Kaul, R. et al. In: Program and abstracts of the 7th Conference on Retroviruses and Opportunistic Infections (San Francisco) San Francisco: Foundation for Retrovirology and Human Health, 2000, 168), the hallmark of HIV infection is the almost universal inability of humans to mount an immune response that can prevent the eventual development of AIDS.

An effective vaccine will require not only the design of effective immunogens, but also the design of optimized protocols of immunogen delivery. As a live, attenuated vaccine for HIV is considered difficult to test and dangerous to implement (Nathanson, N. and Mathieson, B. J. 2000 *J Infect Dis* 182:579-589; Cho, M. W. 2000 *Adv Pharmacol* 49:263-314; Baba, T. W. et al. 1999 *Nat Med* 5:194-203; Baba, T. W. et al. 1995 *Science* 267:1820-1825; Bogers, W. M. et al. 1995 *AIDS* 9:F13-F18; Greenough, T. C. et al. 1999 *N Engl J Med* 340: 236-237; Berkhout, B. et al. 1999 *J Virol* 73:1138-1145), various alternatives to HIV could be considered as potential "live" vectors for HIV immunogens, including enteric bacteria, poxviruses (vaccinia and canarypox), small RNA viruses (e.g. poliovirus and Semliki Forest virus), Rhabdoviruses (e.g. vesicular stomatitis virus), DNA viruses (e.g. adenovirus and adeno-associated viruses) and even naked DNA to achieve expression in living host cells (Cho, M. W. 2000 *Adv Pharmacol* 49:263-314; Rose, N. F. et al. 2001 *Cell* 106:539-549).

Dengue possesses several advantages which favor its choice as a vector for HIV immunogens. As a flavivirus, it replicates entirely in the cytoplasm through RNA directed RNA polymerization and is incapable of integrating into the host genome. Flavivirus replicons can replicate inside cells and achieve prolonged expression of high levels of virally encoded proteins with minimal toxicity (Khromykn, A. A. and Westaway, E. D. 1997 *J Virol* 71(2):1497-1505) and are unable to recombine or mutate to produce infectious HIV particles. Finally, by eliciting an immune reaction against the dengue non-structural proteins remaining in replicons, dengue virus replicons may induce a protective immunity against dengue which would not predispose vaccinated individuals to DHF. Properly administered, dengue virus replicons expressing HIV epitopes might thus serve as dual vaccines, conferring protection against dengue virus as well as HIV.

The challenges in developing a safe and effective HIV vaccine are many and varied. Choice of immunogen is clearly problematic. Critical epitopes may be masked by glycosyl groups and/or tertiary structure (Reitter, J. et al. 1998 *Nat Med* 4:679-684; Chan, D. C. and Kim, P. S. 1998 *Cell* 93:681-684; LaCasse, R. A. et al. 1999 *Science* 283:357-362) and (Cooney, E. L. et al. 1991 *Lancet* 337:567-572). The extensive genetic variability of HIV complicates immunogen choice and the high rate of mutation increases the likelihood of the rapid development of resistance. Furthermore, the method of immunogen delivery (e.g., purified subunits or inactivated virus vs. various forms of "live" expression) can determine the relative nature and extent of humoral and cell mediated immunologic responses. Priming with various types of "live" expression followed by boosting with purified subunits is currently favored as a method to obtain stronger immunologic responses than either method alone (reviewed in Nathanson, N. and Mathieson, B. J. 2000 *J Infect Dis* 182:579-589; and Cho, M. W. 2000 *Adv Pharmacol* 49:263-314). Previously acquired immunity to a viral vector such as vaccinia may influence its efficacy in inducing immunity against heterologous proteins being delivered (Cooney, E. L. et al. 1991 *Lancet* 337:567-572; Cooney, E. L. et al. 1993 *PNAS USA* 90:1882-1886; Graham, B. S. et al. 1992 *J Infect Dis* 166:244-52; McElrath, M. J. et al. 1994 *J Infect Dis* 169:41-47) and it may be wise to provide physicians with HIV vaccines based on a variety of vectors to handle a variety of clinical situations.

The use of live dengue as a vaccine or as a vector for heterologous immunogens has historically been considered problematic because of the pathologies associated with dengue infection. Although dengue fever (DF) is usually self limited, dengue hemorrhagic fever (DHF) is considerably debilitating and frequently fatal (Monath, T. P. 1994 *PNAS USA* 91:2395-2400). However, DHF is unlikely to result from or be promoted by the vectors reported herein. The enhanced replication of virus seen in dengue hemorrhagic fever is generally seen upon reinfection by dengue virus of a serotype different from previous infections and is believed to be mediated by antibodies against viral structural proteins: so called antibody dependent enhancement of infection, or ADE. These cross reacting antibodies actually promote viral uptake by macrophages (Morens, D. M. 1994 *Clin Infect Dis* 19:500-512; Halstead, S. B. 1988 *Science* 239:476-481). The main challenge in using live dengue in humans is thus avoiding the development of antibody dependent enhancement (ADE) of infection by antibodies against the pre-M and E proteins of one dengue strain which weakly cross react with the pre-M and E of a second infecting dengue strain. Since the replicons reported herein lack the major viral structural protein genes, they are not only incapable of sustaining a spreading infection but also are incapable of eliciting antibodies against the missing structural proteins. They should neither induce DF nor promote DHF.

Figure 6:
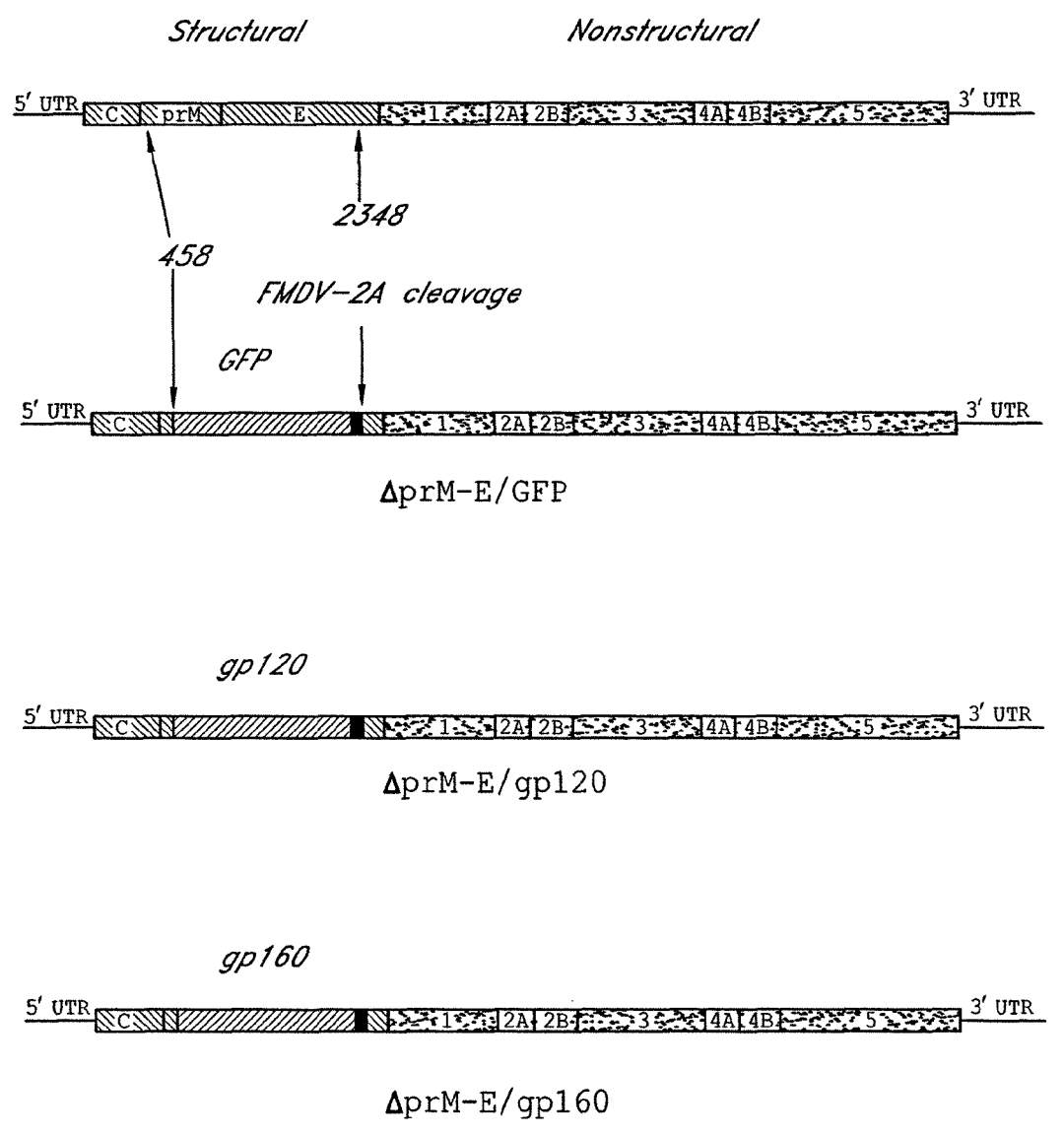

Dengue virus has a typical flavivirus genome structure, as described in FIG. 6. The structural proteins, C, pre-M (M) and E, are involved in packaging, export and subsequent entry. The non-structural proteins, NS1, NS2A, NS2B, NS3, NS4A, NS4B and NS5 include an RNA-directed RNA polymerase and a protease function involved in cleaving certain positions of the long viral polyprotein which contains all the viral genes (Chambers, T. J. et al. 1990 *Ann Rev Microbiol* 44:649-88; Rice, C. M In: *Fields Virology,* 3rd ed. Philadelphia, Pa. Lippincott-Raven Publishers, 1996 p. 931-996). The four serotypes of dengue virus ("1" through "4") share approximately 60%-74% amino acid residue identity with one another in the E gene (Thomas, C. J. et al. 1990 *Annu Rev Microbiol* 44:649-88) and induce cross-reacting antibodies (Heinz, F. X. 1986 *Adv Virus Res* 31:103-168).

Two strategies suggest themselves for circumventing the problem of ADE from dengue vaccination. One strategy is to immunize with multiple strains of dengue virus to elicit high affinity, neutralizing antibodies against the multiple dengue serotypes. At least one vaccine to do this (using dengue vaccine candidates, DEN-1 PDK13, DEN-2 PDK53, DEN-3 PGMK 30/F3, and DEN-4 PDK48) has been in clinical trials (Bhamarapravati, N. and Sutee, Y. 2000 *Vaccine* 18 Suppl 2:44-47; Kanesa-thasan, N. et al. 2001 *Vaccine* 19:3179-3188). A second strategy is to induce immunity only to viral proteins other than pre-M and E. Several studies have shown that the nonstructural glycoprotein NS1 can play an important role in protection against dengue. Mice immunized with purified dengue-2 NS1 protein injected intramuscularly and boosted after 3 days and two weeks were protected from developing lethal dengue encephalitis upon subsequent challenge with dengue-2 virus (Schlesinger, J. J. et al. 1987 *J Gen Virol* 68:853-857). Similarly, mice immunized with recombinant vaccinia virus expressing authentic NS1 (Falgout, B. et al. 1990 *J Virol* 64:4356-4363) were protected against the development of dengue-4 virus encephalitis when challenged by intracerebral injection. Inoculation of mice with specific combinations of monoclonal antibodies (Mabs) directed against dengue-2 NS1 (Henchal, E. A. et al. 1988 *J Gen Virol* 69:2101-2107) also protects against lethal virus encephalitis upon intracerebral dengue-2 challenge. Other nonstructural proteins are also immunogenic and may participate in eliciting protection (Brinton, M. A. et al. 1998 *Clin Diagn Virol* 10:129-39).

Herein we have reported the successful construction of several dengue virus replicons which replicate intracellularly without the pre-M and E proteins required to form infectious virions, including replicons which can be expressed from transfected DNA. Towards the goal of devising a "live" dual vaccine based on only non-structural dengue proteins and heterologous HIV material, we report herein that these replicons can be harnessed to express heterologous genes, including HIV gp160 and gp120. Upon introduction into a host's cells, these sub-genomic fragments should replicate intracellularly and support prolonged expression of dengue and heterologous immunogens without producing the deleted dengue structural proteins and without forming infectious virions.

Development of Dengue Virus Replicons Expressing HIV-1 Gp120 and Other Heterologous Genes: a Tool for Dual Vaccination Against Dengue Virus and HIV (Preface)

Toward the goals of providing an additional vector to add to the armamentarium available to HIV vaccinologists and of creating a bivalent vaccine effective against dengue virus and HIV, we have attempted to create vectors which express dengue virus non-structural proteins and HIV immunogens. Herein we have reported the successful construction of dengue virus replicons which lack structural genes necessary for virion release and spreading infection in culture but which can replicate intracellularly and abundantly produce dengue non-structural proteins. Herein we have now expressed heterologous genetic material from these replicons.

We cloned into a Δpre-M/E dengue virus replicon genes for either green fluorescent protein (GFP), HIV gp160 or HIV gp120 and tested the ability of these constructs to express dengue virus proteins as well as the heterologous proteins in tissue culture after transfection of replicon RNA.

Our conclusions indicate that heterologous proteins were readily expressed from these constructs. GFP and gp120 demonstrated minimal or no toxicity. Gp160 expressing replicons were found to express proteins abundantly at 36 hours post transfection, but after 50 hrs. of transfection, few replicon positive cells could be found despite the presence of cellular debris positive for replicon proteins. This suggested that gp160 expressed from dengue virus replicons is considerably more toxic than either GFP or gp120. The successful expression of heterologous proteins, including HIV gp120 for long periods in culture indicates this vector system should be useful as a vaccine vector, given appropriate delivery methods.

Figure 7:
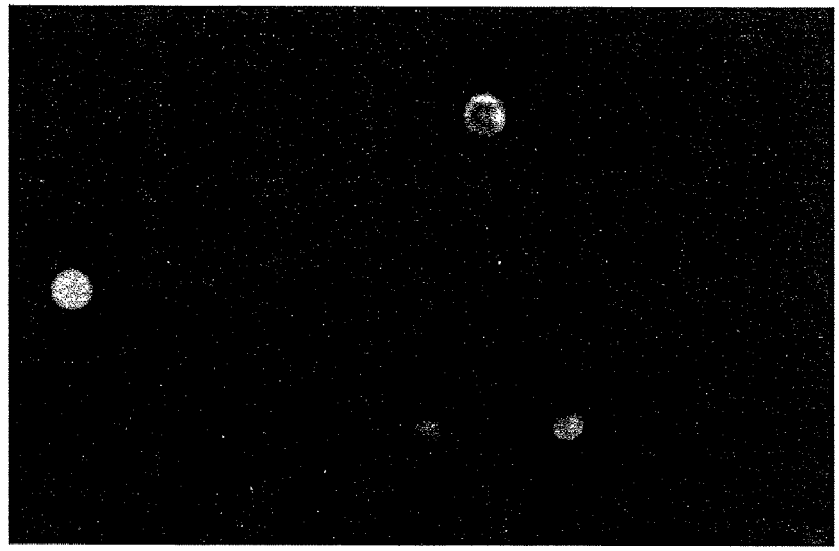
FIG. 7. Expression of green fluorescent protein (GFP) by Δpre-M/E-GFP 48 hours post transfection.

Development of Dengue Virus Replicons Expressing HIV-1 gp120 and Other Heterologous Genes: a Tool for Dual Vaccination Against Dengue Virus and HIV In various previous attempts to express heterologous genes in full length, wild type dengue virus, we experienced a very poor success rate, despite attempts to clone heterologous material into various positions of the genome. Our first efforts to determine whether or not heterologous material could be readily expressed in dengue replicons was to clone the comparatively tractable green fluorescent protein (GFP) into the Δpre-M/E replicon, into the position from which the pre-M and E genes had been deleted (FIG. 6). GFP was readily visualized in cultures 48 hours post transfection with Δpre-M/E-GFP, as seen in FIG. 7.

Figure 8:
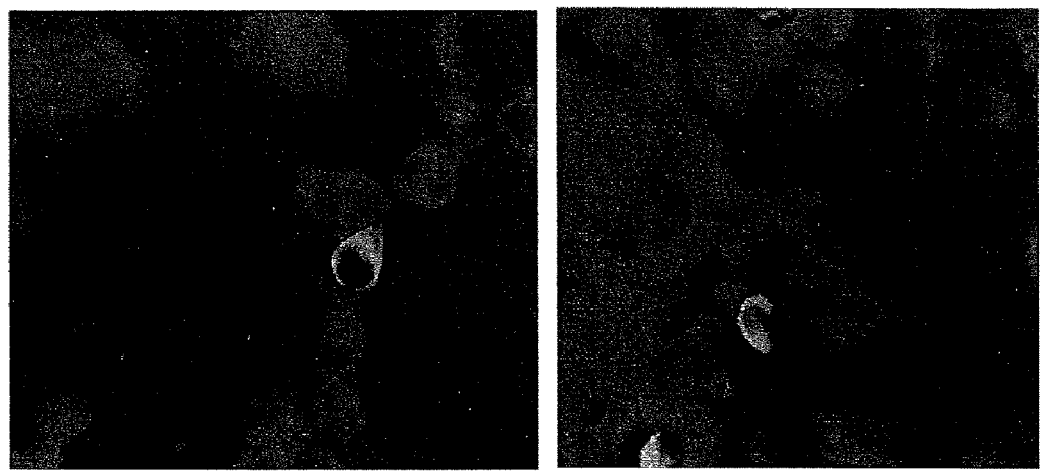
FIG. 8. Expression of proteins by Δpre-M/E-gp120 50 hours post transfection. Left and right frames are two independent fields. Anti-dengue serum was used in these experiments.
Figure 9:
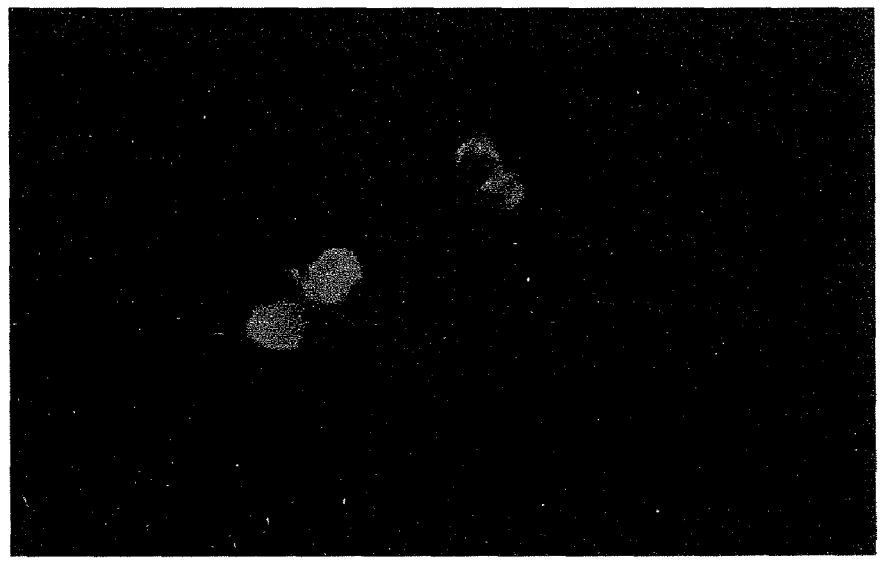
FIG. 9. Expression of proteins by Δpre-M/E-gp120 48 hours post transfection. Left and right frames are two independent fields. Anti-HIV serum was used in these experiments.
Figure 10:
FIG. 10. Expression of gp160 by Δpre-M/E-gp160 48 hours post transfection. Left and right frames are independent fields. Anti-HIV serum was used in these experiments.
Figure 11:
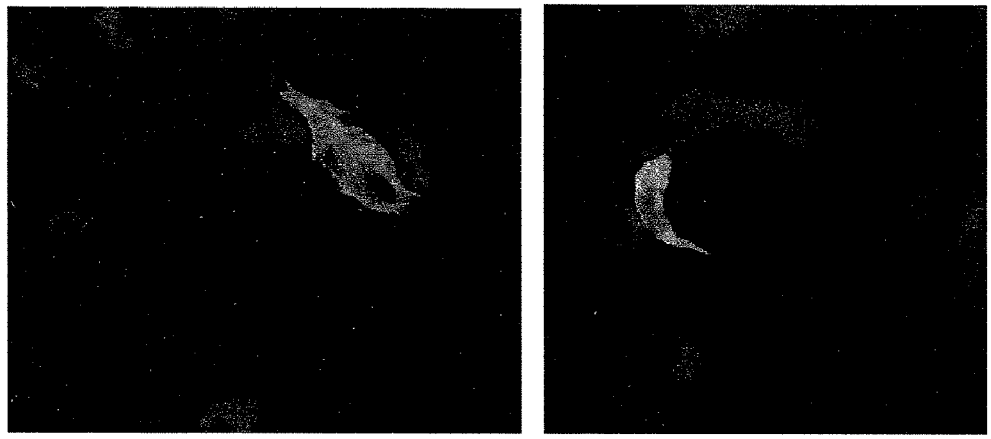
FIG. 11. Expression of gp160 by Δpre-M/E-gp160 36 hours post transfection. Anti-dengue serum was used in these experiments. Left and right panels are independent fields.

Encouraged by the success with GFP, we next looked at Δpre-M/E replicons with HIV-1 env material cloned into the position of the deleted pre-M and E genes. We analyzed two clones, Δpre-M/E-gp120 and Δpre-M/E-gp160, expressing HIV-1 gp120 and gp 160 respectively (FIG. 6). Expression of genes in the Δpre-M/E-gp120 replicon was reproducibly visualized at 48-50 hours post transfection (FIGS. 8 and 9), at a level of approximately 1% of the cells, but in many experiments, the corresponding cultures transfected with the gp160 replicon, Δpre-M/E-gp160, either no fluorescence could be visualized, or only fluorescent cells with a bizarre morphology (characterized by debris and/or degenerative appearance) could be visualized (FIG. 10). However, when we harvested cultures earlier, at 36 hours post transfection with Δpre-M/E-gp160, intact, fluorescing cells were readily found, though the morphology still appeared atypical compared to either that of cultures transfected with wild type dengue virus and dengue replicons or the Δpre-M/E-gp120 replicon (see FIG. 11).

Figure 12:
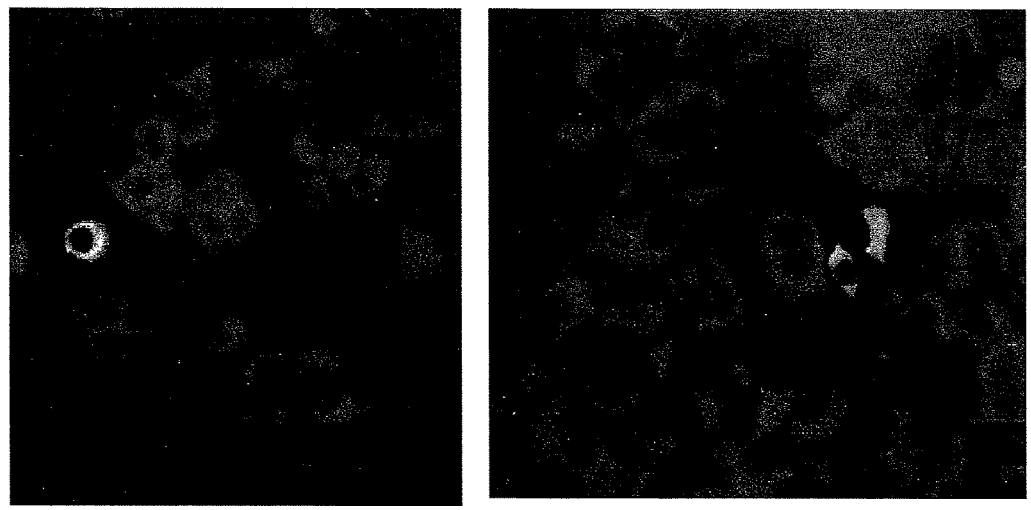
FIG. 12. Expression of proteins by Δpre-M/E-gp120 9 days post transfection. Cells were trypsinized and replated on day 7 post transfection and harvested for immunofluorescence two days later. Left and right frames are two independent fields. Anti-dengue serum was used in these experiments FIG. 13. Simultaneous expression of HIV and dengue proteins by Δpre-M/E-gp120-transfected cells 4 days post transfection. Left frame: FITC detection of HIV proteins. Right frame: Rhodamine detection of dengue proteins.
Figure 13:
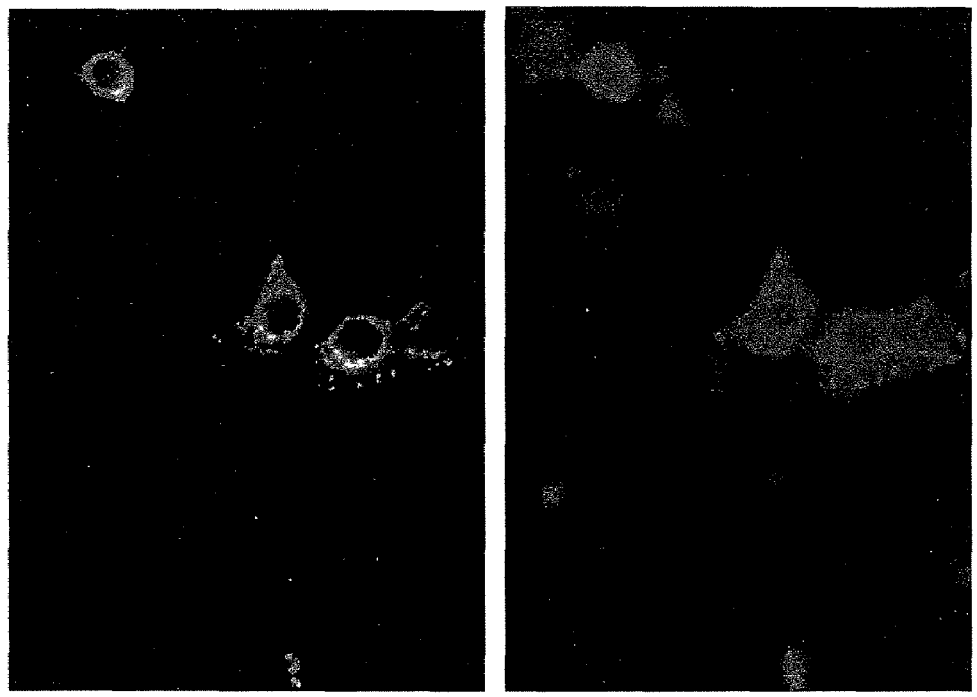
Figure 14:
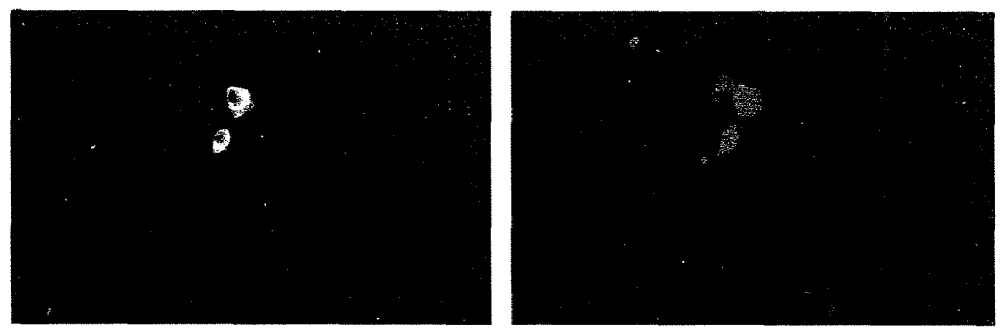
FIG. 14. Simultaneous expression of HIV and dengue proteins by Δpre-M/E-gp120-transfected cells 7 days post transfection. Left frame: FITC detection of HIV proteins. Right frame: Rhodamine detection of dengue proteins.

To serve as effective vaccines, it is preferable, if not necessary, that expression systems be capable of expressing immunogens for longer than a couple of days. Although we knew from previous experiments that dengue replicons could survive for at least 7 days in culture, the limited durability of cells transfected with gp160-expressing replicons raised the question of whether or not cells transfected with Δpre-M/E-gp120 replicons could survive for similarly long times in culture. When cultures transfected with Δpre-M/E-gp120 were trypsinized and replated on day 7 post transfection and then analyzed on day 9 post transfection, fluorescent cells were readily visualized (FIG. 12). In comparison to cultures that were not trypsinized on day 7 post transfection however, these cultures had fewer intact fluorescent cells and more debris. Although this suggests that gp120 expression from a dengue replicon stresses cells, we did find fields with adjacent, gp120 positive cells, suggesting that at least one cell division between day 7 and day 9 had occurred in a cell successfully transfected with Δpre-M/E-gp120 (FIG. 12, right panel). At 9 days of culture post transfection with Δpre-M/E-gp120, only about 0.1% of the cells or less were positive, which represents a considerable decrease from 48 hours post transfection.

In the experiments described above and in FIGS. 8 through 12, expression of dengue replicons with heterologous material from HIV was followed either using anti-HIV sera or anti-dengue sera, depending on the experiment. To demonstrate that the same cells were expressing both dengue proteins and HIV proteins, we used a double label technique, with FITC detecting HIV proteins and rhodamine detecting dengue proteins. FIG. 13 demonstrates the concordance of dengue virus protein and gp120 expression in cultures 4 days post transfection with Δpre-M/E-gp120 (FIG. 13). The more extensive background of auto fluorescence encountered when visualizing the rhodamine fluorescence makes low levels of specific rhodamine fluorescence more difficult to discern, but clearly all intact cells positive for HIV are also positive for dengue proteins. The rhodamine-positive spot in the lower left of the panel is cellular debris and is also positive for dengue proteins, but the FITC fluorescence was not well reproduced by digital photography, though it still may be visualized on certain monitor/computer combinations. Similar results were obtained at 7 days post transfection (FIG. 14).

Our finding that dengue virus replicons can express heterologous genes, including HIV envelope, for prolonged periods of time in cell culture without selection represents a significant step in developing a new vector system potentially capable of delivering immunogens to any host in whose cells the dengue replicons can replicate. Flavivirus replicons have previously been demonstrated to express heterologous genes for up to 41 days in tissue culture in Kunjin (Khromykn, A. A. and Westaway, E. D. 1997 *J Virol* 71:1497-1505). However, these experiments were done in the presence of selection for the heterologous genes cloned into the replicons. We have demonstrated heterologous gene expression in the absence of selection for up to at least 9 days post transfection with chimeric dengue replicons. Although we have formally demonstrated expression, not replication, our previous demonstration of the replication of dengue replicons lacking heterologous material suggests that the replicons described herein, which contain heterologous material, are indeed replicating. Evidence that cells continue to replicate and express replicon proteins in both daughter cells after transfection with these chimeric replicons further supports the implication of chimeric replicon replication. Ideally, to serve as dual vaccines against dengue as well as against other pathogens, the replicons should express the dengue NS1 protein (Schlesinger, J. J. et al. 1987 *J Gen Virol* 68:853-857; Falgout, B. et al. 1990 *J Virol* 64:4356-4363; Henchal, E. A. et al. 1988 *J Gen Virol* 69:2101-2107; Brinton, M. A. et al. 1998 *Clin Diagn Virol* 10:129-39). So far, attempts to visualize NS1 production by Western blots have failed, presumably because of the low transfection efficiencies. However, we have previously argued that the replication of dengue replicons could not take place in the absence of the essential non-structural gene, NS1, which implies that NS1 is being made. The frequencies and fluorescence intensities of replicon positive cells seen in the experiments reported herein are comparable to those seen for dengue replicons lacking heterologous material, suggesting that replication of the Δpre-M/E replicons containing heterologous material is occurring as well. The finding of at least one closely apposed pair of cells expressing high levels of replicon proteins on day 9 post transfection, two days after trypsinization and replating (FIG. 12, right panel), not only implies replicon replication, but also implies the expression of NS-1 protein as well. We contemplate the definitive demonstration of effective NS-1 production upon studies of the immune response in animals immunized with these replicons.

Choice of immunogen remains problematic for these vectors. Clearly, HIV-1 gp 160 is too toxic for prolonged expression. Even the gp120-expressing replicon seems mildly toxic in that the frequency of gp120 positive cells declines with time in culture post transfection with Δpre-M/E-gp120. However, as noted above, we have seen at least one instance of putative cellular division at least 7 days after being successfully transfected by Δpre-M/E-gp120 (FIG. 12, right panel). Experiments are contemplated to determine the feasibility of long term expression of other HIV-1 immunogens, including gag and tat.

In conclusion, demonstration of long term protein expression by a gp120-expressing replicon alone, of course, does not demonstrate that the chimeric dengue replicons constitute an effective vaccine. However, at the very least they add to the potential armamentarium available to the vaccinologist. It is highly likely that a successful HIV vaccination protocol will involve multiple immunogens and delivery protocols. For instance, mice immunized with attenuated Friend leukemia virus (FLV) develop an immune response whose efficacy is dependent on the additive effects of at least three separable spleen cell populations (Dittmer, U. et al. 1999 *J Virol* 73:3753-3757). By analogy, it may be necessary to devise multiple strategies to obtain a similarly complex and effective immune response in humans against HIV. In animal models of HIV, different immunogens and modes of immunization can induce different modes of protection with varying degrees of effectiveness (Heeney, J. et al. 1999 *Immunol Lett* 66:189-95; Hirsch, V. et al. 1996 *J Virol* 70:3741-3752; Quesada-Rolander, M. et al. 1996 *AIDS Res Hum Retroviruses* 12:993-999; Letvin, N. L. et al 1997 *PNAS USA* 94:9378-383; Miller, C. J. et al. 1997 *J Virol* 71:1911-1921; Shibata, R. et al. 1997 *J Virol* 71:8141-8148; Gundlach, B. et al. 1998 *J Virol* 72:7846-7851). Harnessing multiple immune responses may be the answer to designing an effective HIV vaccine (Nathanson, N. and Mathieson, B. J. 2000 *J Infect Dis* 182: 579-589) and the availability of multiple vectors should facilitate the harnessing of multiple responses.

Culturing of Dengue Virus

Dengue virus strains DEN1/WP and DEN2/NGC, kindly provided by Dr. Lewis Markoff, (Polo, S. et al. 1997 *J Virol* 71:5366-5374; Pur, B. et al. 2000 *Virus Genes* 20:57-63) were passaged in monkey LLC-MK2 cells at 37° C. in a humidified incubator under 5% $CO_2$, using Medium 199 plus 10% fetal bovine serum (FBS) and 50 μg of Gentamicin per ml. The cells were trypsinized a day before virus infection and plated to reach approximately 80% confluence on the day of infection. Infections were typically at an MOI of 0.01 PFU/cell in Medium 199 plus 2% FBS.

In Vitro Mutagenesis

Heterologous genes were cloned into the previously described Δpre-M/E replicon, into the position previously occupied by the pre-M/E genes. DNA fragments used for desired regions of heterologous genes (see FIG. 6) were synthesized by polymerase chain reaction (PCR) from short overlapping primers. For the Green Fluorescent Protein (GFP) gene, the 5' primer was 5'CGAAAAAAGGC-GAGAAATACGCCTTTCAATATGCTGAA ACGC-GAGAGAATGGTGAGCAAGGGCGAGGAGCTG3' (SEQ ID. NO.: 26) and the 3' primer was 5'AAGGTCAAAAT-TCAACAGCTGCTTGTACAGCTCGTCCATGCC3' (SEQ ID. NO.: 27). For HIV-1 gp120 gene, the 5' primer was 5'ATCATTATGCTGAAT CCAACAGTGATGGCGTTC-CATTTACCACACGTAACATGAGAGTGATGGGGATCA GGAAG3' (SEQ ID. NO.: 28) and the 3' primer was 5'AAG-GTCAAAATTCAACAGCTG GGTGGGTGCTAATC-CTAATGGTTC3' (SEQ ID. NO.: 29). GFP and HIV-1 gp120 were fused with FMDV/2A self cleaving protein sequence to replace natural cleavage sites in the dengue polyprotein. These sites seem to loose their activity when juxtaposed with heterologous material. PCR was used to amplify DNA coding for the FMDV/2A self cleaving protein. The 5' primer was 5'CAGCTGTTGAATTTTGACCTTCTTAAGCTTG CGG-GAGACGTCGAGTCCAACCCTGGCCCC' (SEQ ID. NO.: 30) and the 3' primer was

```
                                        (SEQ ID. NO.: 31)
5'ATACAGCGTCACGACTCCCACCAATACTAGTGACACAGACAGTGAGGT

GCTGGGGCCAGGGTTGGACTCGAC3'.
```

Dengue-2 virus cDNA cloned in the yeast shuttle vector pRS424, linearized by excision of a short Bam H1 fragment was transfected into competent (Spencer, F. et al. 1993 *Methods Companion Methods Enzymol* 5:161-175) *S. cerevisiae* YPH857, kindly provided by Barry Falgout (CBER/FDA), along with the appropriate PCR fragment spanning the desired deletion. Yeast colonies which grew on tryptophan minus plates represented vectors which had recircularized by homologous recombination with these PCR fragments (Hirsch, V. et al. 1996 *J Virol* 70:3741-3752). DNA from these colonies was transformed into *E. coli* STBL 2 cells (Life Technologies, Inc.) to make sufficient quantities of dengue recombinant, genomic-length DNAs for characterization and analysis.

Expression of Virus and Replicons in Cells

The full length virus and replicon cDNA plasmids isolated from STBL 2 cells were linearized with SacI, purified by Qiagen chromatography, and eluted by RNAase-free water in preparation for transcription. The transcription reaction mixtures contained 1 μg of linearized DNA; 0.5 mM (each) ATP, CTP, and UTP; 0.1 mM GTP; 0.5 mM cap analog (NEBL); 10 mM DTT; 40 U of Rnasin (Promega); 30 U of SP6 RNA polymerase; and 1×SP6 RNA polymerase buffer (Promega) in a volume of 30 μl. The reaction mixtures were incubated at 40° C. for 2 hr. Aliquots (12.5 μl) of the reaction mixtures, containing full length viral RNA, were used to transfect approximately $2\times10^6$ Monkey LLC-MK2 cells in phosphate-buffered saline (PBS) by electroporation in a 0.4 cm gap electroporation cuvette. Each cuvette was pulsed at 200 V, 950 μF using a BioRad Genepuls electroporator. The cells were then resuspended in growth medium and plated on the appropriate tissue culture dish.

After electroporation, cells were either plated directly on multiwell plates for harvest at short time periods (typically 4 days or less) or on tissue culture dishes for trypsinization and seeding onto multiwell plates one or two days before final harvest for longer time periods.

Immuno-Histochemical Methods

For immunofluorescent detection of dengue-specific proteins, cells growing on chamber slides were rinsed in room-temperature PBS and then fixed in cold acetone for 10 min at −20° C. After being air dried, each chamber was covered with 50 μl of a 1:50 dilution of DEN2-specific hyperimmune mouse ascitic fluid (HMAF, American Type Culture Collection) in PBS plus 2% normal goat serum and incubated at room temperature for 1 h in a humidified atmosphere and then rinsed twice in PBS. After washing, cells were subsequently incubated with a 1:100 dilution of fluorescein isothiocyanate-labeled goat anti-mouse antibodies (Kirkegaard and Perry Laboratory) and rinsed twice in PBS. For detection of HIV-specific proteins, the same protocol was used except that cells were initially incubated with human HIV-1 serum from Waldheim Pharmazeutika Ges.m.b.H. Neufeld-Vienna, Austria and then subsequently incubated with fluorescent-labeled goat anti-human antibody. Cells in some, but not all experiments were counterstained with 0.02% Evans Blue.

For dual labeling, the first antibodies were a 1:50 dilution of dengue type 2 specific hyperimmune mouse ascitic fluid (HMAF, American type culture collection) and a 1:100 dilution of human HIV positive serum in PBS plus 2% normal goat serum. The second antibodies were a 1:100 dilution of FITC-labeled goat anti-human antibodies (Waldeim Pharmazeutika) and a 1:50 dilution of goat anti-mouse IgG-L-Rhodamine (Boehringer Mannheim Biochemicals).

While the present invention has been described in some detail for purposes of clarity and understanding, one skilled in the art will appreciate that various changes in form and detail can be made without departing from the true scope of the invention. All patents, patent applications and publications referred to above are hereby incorporated by reference.

What is claimed is:

1. A subgenomic replicon of dengue virus origin comprising a deletion for the sequence coding for C.

2. The subgenomic replicon of claim 1 wherein the dengue virus origin is dengue virus type 1, 2, 3 or 4 origin.

3. The subgenomic replicon of dengue virus origin of claim 1 which is adapted to receive at least a nucleotide sequence without disrupting its replication capabilities.

4. The subgenomic replicon of dengue virus origin of claim 1 comprising a deletion for the sequence coding for C, PreM, and E structural proteins (ΔCME); and further comprising part or all of the 5'UTR; at least about the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, or 175 nucleotides of C protein; at least about the last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, or 175 nucleotides of E protein; substantially all of the nonstructural region; and part or all of the 3'UTR.

5. The subgenomic replicon of claim 4 wherein the dengue virus origin is dengue virus type 1, 2, 3 or 4 origin.

6. A vaccine comprising the subgenomic replicon of dengue virus origin of claim 1, optionally which is adapted to receive at least a nucleotide sequence without disrupting its replication capabilities, and a pharmaceutically acceptable carrier.

7. A therapeutic comprising the subgenomic replicon of dengue virus origin of claim 3 and a pharmaceutically acceptable carrier.

8. A dengue virus like particle comprising a subgenomic replicon of dengue virus origin of claim 3 further comprising structural proteins of the homologous dengue virus wherein said structural proteins encapsulate said subgenomic replicon.

9. A method of immunization comprising administering to an individual in need thereof a subgenomic replicon of dengue virus origin of claim 3.

10. A method of treatment comprising administering to an individual in need thereof the subgenomic replicon of dengue virus origin of claim 3.

11. A method of immunization comprising administering to an individual in need thereof a dengue virus like particle of claim 8.

12. A method of treatment comprising administering to an individual in need thereof a dengue virus like particle of claim 8.

13. A subgenomic replicon of dengue virus origin comprising a deletion for the sequence coding for C, PreM, and E structural proteins (ΔCME), or for PreM and E structural proteins (ΔME); and further comprising part or-all of the 5'UTR; at least the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, or 175 nucleotides of C protein; at least the last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, or 175 nucleotides of E protein; substantially all of the nonstructural region; and part or all of the 3'UTR.

14. The subgenomic replicon of claim 13 wherein the dengue virus origin is dengue virus type 1, 2, 3 or 4 origin.

15. The subgenomic replicon of dengue virus origin of claim 13 which is adapted to receive at least a nucleotide sequence without disrupting its replication capabilities.

16. A vaccine comprising the subgenomic replicon of dengue virus origin of claim 13, optionally which is adapted to receive at least a nucleotide sequence without disrupting its replication capabilities, and a pharmaceutically acceptable carrier.

17. A therapeutic comprising the subgenomic replicon of dengue virus origin of claim 15 and a pharmaceutically acceptable carrier.

18. A dengue virus like particle comprising a subgenomic replicon of dengue virus origin of claim 15 further comprising structural proteins of the homologous dengue virus wherein said structural proteins encapsulate said subgenomic replicon.

19. A method of immunization comprising administering to an individual in need thereof a subgenomic replicon of dengue virus origin of claim 15.

20. A method of treatment comprising administering to an individual in need thereof the subgenomic replicon of dengue virus origin of claim 15.

21. A method of immunization comprising administering to an individual in need thereof a dengue virus like particle of claim 18.

22. A method of treatment comprising administering to an individual in need thereof a dengue virus like particle of claim 18.

23. A subgenomic replicon of dengue virus origin comprising a deletion for the sequence coding for ΔCME.

24. The subgenomic replicon of claim 23 wherein the dengue virus origin is dengue virus type 1, 2, 3 or 4 origin.

25. The subgenomic replicon of dengue virus origin of claim 23 which is adapted to receive at least a nucleotide sequence without disrupting its replication capabilities.

26. A vaccine comprising the subgenomic replicon of dengue virus origin of claim 23, optionally which is adapted to receive at least a nucleotide sequence without disrupting its replication capabilities, and a pharmaceutically acceptable carrier.

27. A therapeutic comprising a subgenomic replicon of dengue virus origin of claim 25 and a pharmaceutically acceptable carrier.

28. A dengue virus like particle comprising a subgenomic replicon of dengue virus origin of claim 25 further comprising structural proteins of the homologous dengue virus, wherein said structural proteins encapsulate said subgenomic replicon.

29. A method of immunization comprising administering to an individual in need thereof a subgenomic replicon of dengue virus origin of claim 25.

30. A method of immunization comprising administering to an individual in need thereof a dengue virus like particle of claim 28.

31. A method of treatment comprising administering to an individual in need thereof a subgenomic replicon of dengue virus origin of claim 25.

* * * * *